(12) United States Patent
Razzaque et al.

(10) Patent No.: US 7,728,868 B2
(45) Date of Patent: Jun. 1, 2010

(54) SYSTEM AND METHOD OF PROVIDING REAL-TIME DYNAMIC IMAGERY OF A MEDICAL PROCEDURE SITE USING MULTIPLE MODALITIES

(75) Inventors: Sharif A. Razzaque, Chapel Hill, NC (US); Kurtis P. Keller, Hillsborough, NC (US); Andrei State, Chapel Hill, NC (US); Caroline K. Green, Chapel Hill, NC (US); Jeremy D. Ackerman, Port Jefferson Station, NY (US)

(73) Assignee: Inneroptic Technology, Inc., Hillsborough, NC (US)

( * ) Notice: Subject to any disclaimer, the term of this patent is extended or adjusted under 35 U.S.C. 154(b) by 0 days.

(21) Appl. No.: 11/833,134

(22) Filed: Aug. 2, 2007

(65) Prior Publication Data

US 2008/0030578 A1    Feb. 7, 2008

Related U.S. Application Data

(60) Provisional application No. 60/834,932, filed on Aug. 2, 2006, provisional application No. 60/856,670, filed on Nov. 6, 2006.

(51) Int. Cl.
*H04N 7/18* (2006.01)
(52) U.S. Cl. ........................................ 348/77
(58) Field of Classification Search ........................ None
See application file for complete search history.

(56) References Cited

U.S. PATENT DOCUMENTS 4,294,544 A    10/1981    Altschuler et al.

| 4,884,219 A | 11/1989 | Waldren |
| 5,109,276 A | 4/1992 | Nudelman et al. |
| 5,193,120 A | 3/1993 | Gamache et al. |
| 5,249,581 A | 10/1993 | Horbal et al. |

(Continued)

FOREIGN PATENT DOCUMENTS

CN    1636520    7/2005

(Continued)

OTHER PUBLICATIONS

"3D Laparoscope," copyright 2007 InnerOptic Technology Inc., 2 pages.

(Continued)

*Primary Examiner*—Nhon T Diep
(74) *Attorney, Agent, or Firm*—Knobbe Martens Olson & Bear

(57) ABSTRACT

A system and method of providing composite real-time dynamic imagery of a medical procedure site from multiple modalities which continuously and immediately depicts the current state and condition of the medical procedure site synchronously with respect to each modality and without undue latency is disclosed. The composite real-time dynamic imagery may be provided by spatially registering multiple real-time dynamic video streams from the multiple modalities to each other. Spatially registering the multiple real-time dynamic video streams to each other may provide a continuous and immediate depiction of the medical procedure site with an unobstructed and detailed view of a region of interest at the medical procedure site at multiple depths. As such, a surgeon, or other medical practitioner, may view a single, accurate, and current composite real-time dynamic imagery of a region of interest at the medical procedure site as he/she performs a medical procedure, and thereby, may properly and effectively implement the medical procedure.

29 Claims, 8 Drawing Sheets

U.S. PATENT DOCUMENTS

| | | | |
|---|---|---|---|
| 5,261,404 A | 11/1993 | Mick et al. |
| 5,307,153 A | 4/1994 | Maruyama et al. |
| 5,323,002 A | 6/1994 | Sampsell et al. |
| 5,371,543 A | 12/1994 | Anderson |
| 5,446,798 A | 8/1995 | Morita et al. |
| 5,452,024 A | 9/1995 | Sampsell |
| 5,457,493 A | 10/1995 | Leddy et al. |
| 5,488,431 A | 1/1996 | Gove et al. |
| 5,489,952 A | 2/1996 | Gove et al. |
| 5,491,510 A | 2/1996 | Gove |
| 5,517,990 A | 5/1996 | Kalfas et al. |
| 5,526,051 A | 6/1996 | Gove et al. |
| 5,532,997 A | 7/1996 | Pauli |
| 5,541,723 A | 7/1996 | Tanaka |
| 5,570,135 A | 10/1996 | Gove et al. |
| 5,579,026 A | 11/1996 | Tabata |
| 5,608,468 A | 3/1997 | Gove et al. |
| 5,611,353 A | 3/1997 | Dance et al. |
| 5,612,753 A | 3/1997 | Poradish et al. |
| 5,625,408 A | 4/1997 | Matsugu et al. |
| 5,629,794 A | 5/1997 | Magel et al. |
| 5,630,027 A | 5/1997 | Venkateswar et al. |
| 5,699,444 A | 12/1997 | Palm |
| 5,726,670 A | 3/1998 | Tabata et al. |
| 5,766,135 A | 6/1998 | Terwilliger |
| 5,784,098 A | 7/1998 | Shoji et al. |
| 5,807,395 A | 9/1998 | Mulier et al. |
| 5,820,554 A | 10/1998 | Davis et al. |
| 5,870,136 A | 2/1999 | Fuchs et al. |
| 6,019,724 A | 2/2000 | Gronningsaeter et al. |
| 6,064,749 A | 5/2000 | Hirota et al. |
| 6,095,982 A | 8/2000 | Richards-Kortum et al. |
| 6,167,296 A | 12/2000 | Shahidi |
| 6,216,029 B1 | 4/2001 | Paltieli |
| 6,246,898 B1 | 6/2001 | Vesely et al. |
| 6,261,234 B1 | 7/2001 | Lin |
| 6,341,016 B1 | 1/2002 | Malione |
| 6,348,058 B1 | 2/2002 | Melkent et al. |
| 6,385,475 B1 | 5/2002 | Cinquin et al. |
| 6,442,417 B1 | 8/2002 | Shahidi et al. |
| 6,456,868 B2 | 9/2002 | Saito et al. |
| 6,470,207 B1 | 10/2002 | Simon et al. |
| 6,477,400 B1 | 11/2002 | Barrick |
| 6,478,793 B1 | 11/2002 | Cosman et al. |
| 6,503,195 B1 | 1/2003 | Keller et al. |
| 6,511,418 B2 | 1/2003 | Shahidi et al. |
| 6,518,939 B1 | 2/2003 | Kikuchi |
| 6,527,443 B1 | 3/2003 | Vilsmeier et al. |
| 6,529,758 B2 | 3/2003 | Shahidi |
| 6,546,279 B1 | 4/2003 | Bova et al. |
| 6,551,325 B2 | 4/2003 | Neubauer et al. |
| 6,570,566 B1 | 5/2003 | Yoshigahara |
| 6,587,711 B1 | 7/2003 | Alfano et al. |
| 6,591,130 B2 | 7/2003 | Shahidi |
| 6,594,517 B1 | 7/2003 | Nevo |
| 6,597,818 B2 | 7/2003 | Kumar et al. |
| 6,689,067 B2 | 2/2004 | Sauer et al. |
| 6,725,082 B2 | 4/2004 | Sati et al. |
| 6,733,458 B1 | 5/2004 | Steins et al. |
| 6,766,184 B2 | 7/2004 | Utzinger et al. |
| 6,768,496 B2 | 7/2004 | Bieger et al. |
| 6,782,287 B2 | 8/2004 | Grzeszczuk et al. |
| 6,783,524 B2 | 8/2004 | Anderson et al. |
| 6,827,723 B2 | 12/2004 | Carson |
| 6,873,867 B2 | 3/2005 | Vilsmeier |
| 6,881,214 B2 | 4/2005 | Cosman et al. |
| 6,915,150 B2 | 7/2005 | Cinquin et al. |
| 6,917,827 B2 | 7/2005 | Kienzle, III |
| 6,923,817 B2 | 8/2005 | Carson et al. |
| 6,947,783 B2 | 9/2005 | Immerz |
| 7,033,360 B2 | 4/2006 | Cinquin et al. |
| 7,072,707 B2 | 7/2006 | Galloway, Jr. et al. |
| 7,110,013 B2 | 9/2006 | Ebersole et al. |
| 7,209,776 B2 | 4/2007 | Leitner |
| 7,248,232 B1 | 7/2007 | Yamazaki et al. |
| 7,331,932 B2 | 2/2008 | Leitner |
| 7,385,708 B2 | 6/2008 | Ackerman et al. |
| 7,392,076 B2 | 6/2008 | Moctezuma de La Barrera |
| 7,398,116 B2 | 7/2008 | Edwards |
| 7,480,533 B2 | 1/2009 | Cosman et al. |
| 2001/0007919 A1 | 7/2001 | Shahidi |
| 2001/0045979 A1 | 11/2001 | Matsumoto et al. |
| 2002/0010384 A1 | 1/2002 | Shahidi et al. |
| 2002/0077540 A1 | 6/2002 | Kienzle, III |
| 2002/0077543 A1 | 6/2002 | Grzeszczuk et al. |
| 2002/0138008 A1 | 9/2002 | Tsujita et al. |
| 2002/0198451 A1 | 12/2002 | Carson |
| 2003/0164172 A1 | 9/2003 | Chumas et al. |
| 2003/0231789 A1 | 12/2003 | Willis et al. |
| 2004/0034313 A1 | 2/2004 | Leitner |
| 2004/0095507 A1* | 5/2004 | Bishop et al. ............... 348/441 |
| 2004/0181144 A1 | 9/2004 | Cinquin et al. |
| 2004/0215071 A1 | 10/2004 | Frank et al. |
| 2004/0238732 A1 | 12/2004 | State et al. |
| 2004/0243148 A1 | 12/2004 | Wasielewski |
| 2005/0085717 A1 | 4/2005 | Shahidi |
| 2005/0085718 A1 | 4/2005 | Shahidi |
| 2005/0090742 A1 | 4/2005 | Mine et al. |
| 2005/0111733 A1* | 5/2005 | Fors et al. ................... 382/173 |
| 2005/0192564 A1 | 9/2005 | Cosman et al. |
| 2005/0219552 A1 | 10/2005 | Ackerman et al. |
| 2005/0222574 A1 | 10/2005 | Giordano et al. |
| 2005/0251148 A1 | 11/2005 | Friedrich et al. |
| 2006/0004275 A1* | 1/2006 | Vija et al. ................... 600/407 |
| 2006/0036162 A1 | 2/2006 | Shahidi et al. |
| 2006/0052792 A1 | 3/2006 | Boettiger et al. |
| 2006/0184040 A1 | 8/2006 | Keller et al. |
| 2006/0229594 A1 | 10/2006 | Francischelli et al. |
| 2006/0235290 A1 | 10/2006 | Gabriel et al. |
| 2006/0235538 A1 | 10/2006 | Rochetin et al. |
| 2006/0271056 A1 | 11/2006 | Terrill-Grisoni et al. |
| 2006/0282023 A1 | 12/2006 | Leitner |
| 2007/0167699 A1* | 7/2007 | Lathuiliere et al. .......... 600/407 |
| 2007/0167701 A1 | 7/2007 | Sherman |
| 2007/0167801 A1 | 7/2007 | Webler et al. |
| 2007/0225553 A1 | 9/2007 | Shahidi |
| 2007/0239281 A1 | 10/2007 | Gotte et al. |
| 2007/0244488 A1 | 10/2007 | Metzger et al. |
| 2007/0270718 A1 | 11/2007 | Rochetin et al. |
| 2007/0276234 A1 | 11/2007 | Shahidi |
| 2008/0004516 A1 | 1/2008 | DiSilvestro et al. |
| 2008/0030578 A1 | 2/2008 | Razzaque et al. |
| 2008/0051910 A1 | 2/2008 | Kammerzell et al. |
| 2008/0091106 A1 | 4/2008 | Kim et al. |
| 2008/0161824 A1 | 7/2008 | McMillen |
| 2008/0200794 A1 | 8/2008 | Teichman et al. |
| 2008/0208081 A1 | 8/2008 | Murphy et al. |
| 2008/0214932 A1 | 9/2008 | Mollard et al. |
| 2008/0287805 A1 | 11/2008 | Li |

FOREIGN PATENT DOCUMENTS

| | | |
|---|---|---|
| CN | 100381108 | 4/2008 |
| EP | 1955284 | 8/2008 |
| JP | 2005-058584 | 3/2005 |
| JP | 2005-323669 | 11/2005 |
| JP | 2009-517177 | 4/2009 |
| WO | WO 2007-067323 A2 | 6/2007 |
| WO | WO 2007-067323 A3 | 9/2007 |
| WO | PCT/US2009/032028 | 1/2009 |

OTHER PUBLICATIONS

"RUE: Registered Ultrasound-Endoscope," copyright 2007 InnerOptic Technology, Inc., 2 pages.

"Olympus Endoscopic Ultrasound System," www.olympusamerica. com/msg_section/download_brochures/135_b_gfum130.pdf, printed Sep. 20, 2007, 20 pages.

Michael Bajura et al., "Merging Virtual Objects with the Real World: Seeing Ultrasound Imagery within the Patient," Computer Graphics, Proceedings of SIGGRAPH 1992, vol. 26(2), pp. 203-210, available from www.cs.unc.edu/~fuchs/publications/MergVirtObjs92.pdf, printed Sep. 20, 2007, 8 pages.

Jean-Yves Bouguet, "Camera Calibration Toolbox for Matlab," www.vision.caltech.edu/bouguetj/calib_doc, printed Sep. 20, 2007, 5 pages.

Henry Fuchs et al., "Augmented Reality Visualization for Laparoscopic Surgery," Proceedings of Medical Image Computing and Computer-Assisted Intervention (MICCAI) 1998, pp. 934-943, available from www.cs.unc.edu/~fuchs/publications/AugRealVis_LaparoSurg98.pdf, printed Sep. 20, 2007, 10 pages.

William F. Garrett et al., "Real-Time Incremental Visualization of Dynamic Ultrasound Volumes Using Parallel BSP Trees," Proceedings of IEEE Visualization 1996, pp. 235-240, available from www.cs.unc.edu/~andrei/pubs/1996_VIS_dualBSP_Mac.pdf, printed Sep. 20, 2007, 7 pages.

Marco C. Jacobs et al., "Managing Latency in Complex Augmented Reality Systems," ACM SIGGRAPH Proceedigns of the Symposium of Interactive 3D Graphics 1997, pp. 49-54, available from www.cs.unc.edu/~us/Latency/ManagingRelativeLatency.html, printed Sep. 20, 2007, 12 pages.

Amir Lass, "Assessment of Ovarian Reserve," Human Reproduction, 2004, vol. 19(3), pp. 467-469, available from http://humrep.oxfordjournals.org/cgi/reprint/19/3/467, printed Sep. 20, 2007, 3 pages.

Mark A. Livingston et al., "Magnetic Tracker Calibration for Improved Augmented Reality Registration," Presence: Teleoperators and Virtual Environments, 1997, vol. 6(5), pp. 532-546, available from www.cs.unc.edu/~andrei/pubs/1997_Presence_calibr.pdf, printed Sep. 20, 2007, 14 pages.

E. David Crawford et al., "Computer Modeling of Prostate Biopsy: Tumor Size and Location—Not Clinical Significance—Determine Cancer Detection," Journal of Urology, Apr. 1998, vol. 159(4), pp. 1260-1264, 5 pages.

Michael Meehan et al., "Effect of Latency on Presence in Stressful Virtual Environments," Proceedings of IEEE Virtual Reality 2003, pp. 141-148, available from http://wwwx.cs.unc.edu/~eve/pubs.html, printed Sep. 20, 2007, 8 pages.

Michael Rosenthal et al., "Augmented Reality Guidance for Needle Biopsies: A Randomized, Controlled Trial in Phantoms," Proceedings of MICCAI 2001, eds. W. Niessen and M. Viergever, Lecture Notes in Computer Science, 2001, vol. 2208, pp. 240-248, available from www.cs.unc.edu/~us/AugmentedRealityAssistance.pdf, printed Sep. 20, 2007, 9 pages.

Michael Rosenthal et al., "Augmented Reality Guidance for Needle Biopsies: An Initial Randomized, Controlled Trial in Phantoms," Proceedings of Medical Image Analysis, Sep. 2002, vol. 6(3), pp. 313-320, available from www.cs.unc.edu/~fuchs/publications/AugRealGuida_NeedleBiop02.pdf, printed Sep. 20, 2007, 8 pages.

Andrei State et al., "Case Study: Observing a Volume Rendered Fetus within a Pregnant Patient," Proceedings of IEEE Visualization 1994, pp. 364-368, available from www.cs.unc.edu/~fuchs/publications/cs-ObservVolRendFetus94.pdf, printed Sep. 20, 2007, 5 pages.

Andrei State, et al., "Interactive Volume Visualization on a Heterogenous Message-Passing Multicomputer," Proceedings of 1995 Symposium on Interactive 3D Graphics, 1995, pp. 69-74, 208, available from www.cs.unc.edu/~andrei/pubs/1995_I3D_vol2_Mac.pdf, printed Sep. 20, 2007, 7 pages.

Andrei State et al., "Technologies for Augmented Reality Systems: Realizing Ultrasound-Guided Needle Biopsies," Computer Graphics, Proceedings of SIGGRAPH 1996, pp. 439-446, available from www.cs.unc.edu/~fuchs/publications/TechnoForAug-RealSys96.pdf, printed Sep. 20, 2007, 8 pages.

Andrei State et al., "Superior Augmented Reality Registration by Integrating Landmark Tracking and Magnetic Tracking," ACM SIGGRAPH Computer Graphics, Proceedings of SIGGRAPH 1996, pp. 429-438, available from www.cs.princeton.edu/courses/archive/fall01/cs597d/papers/state96.pdf, printed Sep. 20, 2007, 10 pages.

Andrei State et al., "Simulation-Based Design and Rapid Prototyping of a Parallax-Free, Orthoscopic Video See-Through Head-Mounted Display," Proceedings of International Symposium on Mixed and Augmented Reality (ISMAR) 2005, available from www.cs.unc.edu/~andrei/pubs/2005_ISMAR_VSTHMD_design.pdf, printed Sep. 20, 2007, 4 pages.

"Cancer Facts & Figures 2004," www.cancer.org/downloads/STT/CAFF_finalPWSecured.pdf, copyright 2004 American Cancer Society, Inc., printed Sep. 19, 2007, 60 pages.

Beraldin, J.-A. et al., "Optimized Position Sensors for Flying-Spot Active Triangulation Systems," Proceedings of the Fourth International Conference on 3-D Digital Imaging and Modeling (3DIM), Banff, Alberta, Canada, Oct. 6-10, 2003, pp. 334-341, NRC 47083, copyright 2003 National Research Council of Canada, http://iit-iti.nrc-cnrc.gc.ca/iit-publications-iti/docs/NRC-47083.pdf, printed Sep. 19, 2007, 9 pages.

Blais, F., "Review of 20 Years of Range Sensor Development," Journal of Electronic Imaging, 13(1): 231-240, Jan. 2004, NRC 46531, copyright 2004 National Research Council of Canada, http://iit-iti.nrc-cnrc.gc.ca/iit-publications-iti/docs/NRC-46531.pdf, printed Sep. 19, 2007, 14 pages.

"mike robbins—Computer Vision Research—Stereo Depth Perception," http://www.compumike.com/vision/stereodepth.php, copyright 2007 Michael F. Robbins, printed Sep. 19, 2007, 3 pages.

"DAVID Laserscanner <- Latest News <- Institute for Robotics and Process Control <- Te . . . ," http://www.rob.cs.tu-bs.de/en/news/david, printed Sep. 19, 2007, 1 page.

"3D Laparoscope Technology," http://www.inneroptic.com/tech_3DL.htm, copyright 2007 InnerOptic Technology Inc., printed Sep. 19, 2007, 2 pages.

"Point Grey Research Inc.—Imaging Products—Triclops SDK Samples," http://www.ptgrey.com/products/triclopsSDK/samples.asp, copyright 2007 Point Grey Research Inc., printed Sep. 19, 2007, 1 page.

"laser scanned 3d model Final" video, still image of video attached, http://www.youtube.com/watch?v=DaLgIgmoUf8, copyright 2007 YouTube, LLC, printed Sep. 19, 2007, 2 pages.

Andrei State et al., "*Stereo Imagery from the UNC Augmented Reality System for Breast Biopsy Guidance*" Proc. Medicine Meets Virtual Reality (MMVR) 2003 (Newport Beach, CA, Jan. 22-25, 2003).

Ohbuchi et al. "An Incremental Volume Rendering Algorithm for Interactive 3D Ultrasound Imaging", UNC-CH Computer Science Technical Report TR91-003, (1991).

Takagi et al., "Development of a Stereo Video See-through HMD for AR Systems," IEEE, pp. 68-77 (2000).

Viola et al., "Alignment by Maximization of Mutual Information," International Journal of Computer Vision, vol. 24, No. 2, pp. 1-29 (1997).

Akka, "*Automatic Software Control of Display Parameters for Stereoscopic Graphics Images*," SPIE vol. 1669: Stereoscopic Displays and Applications III, pp. 31-38 (1992).

Azuma, "*A Survey of Augmented Reality*," Presence: Teleoperators and Virtual Environments 6, 4:1-48 (Aug. 1997).

Aylward et al., Intra-Operative 3D Ultrasound Augmentation, Proceedings of the IEEE International Symposium on Biomedical Imaging, Washington, Jul. 2002.

G.D. Dodd et al. "Minimally invasive treatment of malignant hepatic tumors: at the threshold of a major breakthrough." Radiographies 20(1),2000, pp. 9-27.

Herline et al., *Surface Registration for Use in Interactive, Image-Guided Liver Surgery*, Computer Aided Surgery 5:11-17 (2000).

Howard et al., An Electronic Device for Needle Placement during Sonographically Guided Percutaneous Intervention, Radiology 2001; 218:905-911.

Ohbuchi et al., "Incremental Volume Reconstruction and Rendering for 3D Ultrasound Imaging," Visualization in Biomedical Computing, SPIE Proceedings, pp. 312-323, (Oct. 13, 1992).

Ohbuchi, "Incremental Acquisition and Visualization of 3D Ultrasound Images," Ph.D. Dissertation, UNC-CH Computer Science Technical Report TR95—023, (1993).

Aylward et al., *Analysis of the Parameter Space of a Metric for Registering 3D Vascular Images*, in W. Niessen and M. Viergever (Eds.): MICCAI 2001, LNCS 2208, pp. 932-939, 2001.

Aylward et al., *Registration and Analysis of Vascular Images*, International Journal of Computer Vision 55(2/3), 123-138, 2003.

Levy et al., *An Internet-Connected, Patient Specific, Deformable Brain Atlas Integrated into a Surgical Navigation System*, Journal of Digital Imaging, vol. 10, No. 3. Suppl. 1 (August), 1997: pp. 231-237.

Yinghui et al., *Real-Time Deformation Using Modal Analysis on Graphics Hardware*, Graphite 2006, Kuala Lumpur, Malaysia, Nov. 29-Dec. 2, 2006.

Fronheiser et al., *Real-Time 3D Color Doppler for Guidance of Vibrating Interventional Devices*, IEEE Ultrasonics Symposium, pp. 149-152 (2004).

Foxlin et al., *An Inertial Head-Orientation Tracker with Automatic Drift Compensation for Use with HMD's*, in Virtual Reality Software & Technology, Proceedings of the VRST Conference, pp. 159-173, Singapore, Aug. 23-26, 1994.

Nakamoto et al., *3D Ultrasound System Using a Magneto-optic Hybrid Tracker for Augmented Reality Visualization in Laparoscopic Liver Surgery*, in T. Dohi and R. Kikinis (Eds.): MICCAI 2002, LNCS 2489, pp. 148-155, 2002.

Leven et al., *DaVinci Canvas: A Telerobotic Surgical System with Integrated, Robot-Assisted, Laparoscopic Ultrasound Capability*, in J. Duncan and G. Gerig (Eds.): MICCAI 2005, LNCS 3749, pp. 811-818, 2005.

Brian W. Progue et al., "*Analysis of acetic acid-induced whitening of high-grade squamous intraepitheliallesions*," Journal of Biomedical Optics; Oct. 2001; 6(4):397-403.

Cancer Prevention & Early Detection Facts & Figures 2004; National Center for Tobacco-Free Kids; 2004; American Cancer Society; USA.

Depiero et al., "*3-D Computer Vision Using Structured Light: Design, Calibration and Implementation Issues*," The University of Tennessee, pp. 1-46, (1996).

Drascic et al., "*Perceptual Issues in Augmented Reality*," SPIE vol. 2653: Stereoscopic Displays and Virtual Reality Systems III, pp. 123-134 (Feb. 1996).

Buxton et al.; "*Colposcopically directed punch biopsy: a potentially misleading investigation*," British Journal of Obstetrics and Gynecology; Dec. 1991; 98:1273-1276.

van Staveren et al., "*Light Scattering in Intralipid-10% in the wavelength range of 400-1100 nm*," Applied Optics; Nov. 1991; 30(31):4507-4514.

Georgakoudi et al., "*Trimodal spectroscopy for the detection and characterization of cervical precancers in vivo*," American Journal of Obstetrics and Gynecology; Mar. 2002; 186(3):374-382; USA.

Ali et al., "*Near Infrared Spectroscopy and Imaging to Probe Differences in Water Content in Normal and Cancer Human Prostate Tissues*," Technology in Cancer Research & Treatment; Oct. 2004; 3(5):491-497; Adenine Press.

Benavides et al., "*Multispectral digital colposcopy for in vivo detection of cervical cancer*," Optics Express; May 19, 2003; 11(1 0) Optical Society of America; USA.

Kanbara et al., "*A Stereoscopic Video See-through Augmented Reality System Based on Real-time Vision-Based Registration*," Nara Institute of Science and Technology, pp. 1-8 (2000).

Lee et al., "*Modeling Real Objects Using Video See-Through Augmented Reality*," Presence, 11(2):144-157 (Apr. 2002).

Chiriboga et al., "*Infrared Spectroscopy of Human Tissue. IV. Detection of Dysplastic and Neoplastic Changes of Human Cervical Tissue Via Infrared Microscopy*," Cellular and Molecular Biology; 1998; 44(1): 219-229.

Matsunaga et al., "*The Effect of the Ratio Difference of Overlapped Areas of Stereoscopic Images on each Eye in a Teleoperation*," Stereoscopic Displays and Virtual Reality Systems VII, Proceedings of SPIE, 3957:236-243 (2000).

Fahey et al., "*Meta-analysis of Pap Test Accuracy; American Journal of Epidemiology*," 1995 141(7):680-689; The John Hopkins University School of Hygiene and Public Health; USA.

Mitchell et al., "*Colposcopy for the Diagnosis of Squamous Intraepithelial lesions: A metaanalysis*," Obstetrics and Gynecology; Apr. 1998; 91(4):626-631.

Milgram et al., "*Adaptation Effects in Stereo due to Online Changes in Camera Configuration*," SPIE vol. 1669-13, Stereoscopic Displays and Applications III, pp. 1-12 (1992).

Hornung et al., "*Quantitative near-infrared spectroscopy of cervical dysplasia in vivo*," Human Reproduction; 1999; 14(11):2908-2916; European Society of Human Reproduction and Embryology.

Nordstrom et al., "*Identification of Cervical Intraepithelial Neoplasia (CIN) Using UV-Excited Fluorescence and Diffuse-Reflectance Tissue Spectroscopy*," Lasers in Surgery and Medicine; 2001; 29; pp. 118-127; Wiley-Liss, Inc.

Robinett et al., "*A Computational Model for the Stereoscopic Optics of a Head-Mounted Display*," SPIE vol. 1457, Stereoscopic Displays and Applications II, pp. 140-160 (1991).

Rolland et al., "*Towards Quantifying Depth and Size Perception in 3D Virtual Environments*," Presence: Teleoperators and Virtual Environments 4, 1:1-21 (1995).

Cantor et al., "*Cost-Effectiveness Analysis of Diagnosis and Management of Cervical Squamous Intraepithelial Lesions*," Diagnostic Strategies for SILs; Feb. 1998; 91(2):270-277.

Paul A. Viola, Alignment by Maximization of Mutual Information, Ph.D. Dissertation, MIT-Artificial Intelligence Laboratory Technical Report No. 1548 (Jun. 1995).

Watson et al., "*Using Texture Maps to Correct for Optical Distortion in Head-Mounted Displays*," Proceedings of the Virtual Reality Annual Symposium '95, IEEE, pp. 1-7 (1995).

Zitnick et al., "*Multi-Base Stereo Using Surface Extraction*," Visual Interface Inc., (Nov. 24, 1996).

Catalano et al. "*Multiphase helical CT findings after percutaneous ablation procedures for hepatocellular carcinoma.*" Abdom. Imaging, 25(6),2000, pp. 607-614.

Holloway, R.; Registration Error Analysis for Augmented Reality; Presence: Teleoperators and Virtual Environments 6(4), 413—432 (1997).

Azuma, R., Bishop, G.; Improving Static and Dynamic Registration in an Optical See-Through HMO; Proceedings of SIGGRAPH '94, Computer Graphics, Annual Conference Series, 1994, 197—204 (1994).

Fuhrmann, A., Splechtna, R., Pikryl, J.; Comprehensive calibration and registration procedures for augmented reality; Proc. Eurographics Workshop on Virtual Environments 2001,219—228 (2001).

Raij, A.B., Johnsen, K., Dickerson, RF., Lok, B.C., Cohen, M.S., Duerson, M., Pauly, RR, Stevens, A.D., Wagner, P., Lind, D.S.; Comparing Interpersonal Interactions with a Virtual Human to Those with a Real Human; IEEE Transactions on Visualization and Computer Graphics 13(3), 443-457 (2007).

Billinghurst, M., Henrysson, A.; Research Directions in Handheld AR; Int. J. of Virtual Reality 5(2),51-58 (2006).

Michael Deering. "High Resolution Virtual Reality." Proceedings of SIGGRAPH '92, Computer Graphics, 26(2), 1992, pp. 195-202.

Andrei State. "Exact Eye Contact with Virtual Humans." Proc. IEEE International Workshop on Human Computer Interaction 2007 (Rio de Janeiro, Brazil, Oct. 20, 2007), pp. 138-145.

Advertisement, "Inspeck 3DC 3D Capturor," Inspeck 3DC 3D Capturor (www.inspeck.com), 1998.

Advertisement, "Virtual 3D High Speed Non-Contact Surface Perception,"Virtual 3-D Technologies Corporation (www.virtual3dtech.com)., Dec. 21, 1998.

Advertisements, "Virtuoso," Visual Interface, Inc. (www.visint.com), Dec. 21, 1998.

Ultraguide 1000 System, Ultraguide, www.ultraguideinc.com, 1998.

Rolland et al., Towards Quantifying Depth and Size Perception in Virtual Environments, Presence: Teleoperators and Virtual Environments, Winter 1995, vol. 4, Issue 1, pp. 24-49.

PCT, The International Search Report of the International Searching Authority, mailed Sep. 9, 2009, for case PCT/US2009/032028.

PCT. The Written Opinion of the International Searching Authority, mailed Sep. 9, 2009, for case PCT/US2009/032028.

Welch, *Hybrid Self-Tracker: An Inertial/Optical Hybrid Three-Dimensional Tracking System*, University of North Carolina Chapel Hill Department of Computer Science, TR 95-048.

Ware et al., "*Dynamic Adjustment of Stereo Display Parameters*," IEEE Transactions on Systems, Many and Cybernetics, 28(1):1-19 (Publication Date Unknown).

* cited by examiner

SYSTEM AND METHOD OF PROVIDING REAL-TIME DYNAMIC IMAGERY OF A MEDICAL PROCEDURE SITE USING MULTIPLE MODALITIES

RELATED APPLICATIONS

This application claims the benefit of U.S. Provisional Patent Application Ser. No. 60/834,932 entitled "Spatially Registered Ultrasound And Endoscopic Imagery," filed Aug. 2, 2006, and U.S. Provisional Patent Application Ser. No. 60/856,670 entitled "Multiple Depth-Reconstructive Endoscopies Combined With Other Medical Imaging Modalities, And Other Related Technological Details," filed on Nov. 6, 2006, the disclosures of both of which are hereby incorporated herein by reference in their entireties.

FIELD OF THE INVENTION

The present invention is directed to a system and method of providing composite real-time dynamic imagery of a medical procedure site using multiple modalities. One or more of the modalities may provide two-dimensional or three-dimensional imagery.

BACKGROUND OF THE INVENTION

It is well established that minimally-invasive surgery (MIS) techniques offer significant health benefits over their analogous laparotomic (or "open") counterparts. Among these benefits are reduced trauma, rapid recovery time, and shortened hospital stays, resulting in greatly reduced care needs and costs. However, because of limited visibility to certain internal organs, some surgical procedures are at present difficult to perform using MIS. With conventional technology, a surgeon operates through small incisions using special instruments while viewing internal anatomy and the operating field through a two-dimensional monitor. Operating below while seeing a separate image above can give rise to a number of problems. These include the issue of parallax, a spatial coordination problem, and a lack of depth perception. Thus, the surgeon bears a higher cognitive load when employing MIS techniques than with conventional open surgery because the surgeon has to work with a less natural hand-instrument-image coordination.

These problems may be exacerbated when the surgeon wishes to employ other modalities to view the procedure. A modality may be any method and/or technique for visually representing a scene. Such modalities, such as intraoperative laparoscopic ultrasound, would benefit the procedure by providing complementary information regarding the anatomy of the surgical site, and, in some cases, allowing the surgeon to see inside of an organ before making an incision or performing any other treatment and/or procedure. But employing more than one modality is often prohibitively difficult to use. This is particularly the case when the modalities are video streams displayed separately on separate monitors. Even if the different modalities are presented in a picture-in-picture or side-by-side arrangement on the same monitor, it would not be obvious to the surgeon, or any other viewer, how the anatomical features in each video stream correspond. This is so because, the spatial relationship between the areas of interest at the surgical site, for example, surface, tissue, organs, and/or other objects imaged by the different modalities, are not aligned to the same view perspectives. As such, the same areas of interest may be positioned and oriented differently between the different modalities. This is a particular problem for modalities like ultrasound, wherein anatomical features do not obviously correspond to the same feature in optical (or white-light) video.

The problems may be further exacerbated in that the surgical site is not static but dynamic, continually changing during the surgery. For example, in laparoscopic surgery, the organs in the abdomen continually move and reshape as the surgeon explores, cuts, stitches, removes and otherwise manipulates organs and tissues inside the body cavity. Even the amount of gas inside the body cavity (used to make space for the surgical instruments) changes during the surgery, and this affects the shape or position of everything within the surgical site. Therefore, if the views from the modalities are not continuous and immediate, they may not accurately and effectively depict the current state and/or conditions of the surgical site.

While there is current medical imaging technology that superimposes a video stream using one modality on an image dataset from another modality, the image dataset is static and, therefore, not continuous or immediate. As such, the image dataset, must be periodically updated based on the position of the subject, for example the patient, and/or anatomical or other features and/or landmarks. Periodically updating and/or modifying the image dataset may introduce undue latency in the system, which may be unacceptable from a medical procedure standpoint. The undue latency may cause the image being viewed on the display by the surgeon to be continually obsolete. Additionally, relying on the positions of the subject, and/or anatomical or other features and/or landmarks to update and/or modify the image being viewed, may cause the images from the different modalities to not only be obsolete but, also, non-synchronous when viewed.

Accordingly, there currently is no medical imaging technology directed to providing composite real-time dynamic imagery from multiple modalities using two or more video streams, wherein each video stream from each modality may provide a real-time view of the medical procedure site to provide a continuous and immediate view of the current state and condition of the medical procedure site. Also, there currently is no medical imaging technology directed to providing composite imagery from multiple modalities using two or more video streams, wherein each video stream may be dynamic in that each may be synchronized to the other, and not separately to the position of the subject, and/or anatomical or other features and/or landmarks. As such, there is currently no medical imaging technology that provides composite real-time, dynamic imagery of the medical procedure site from multiple modalities.

Therefore, there is a need for a system and method of providing composite real-time dynamic imagery of a medical procedure site from multiple medical modalities, which continuously and immediately depicts the current state and condition of the medical procedure site and does so synchronously with respect to each of the modalities and without undue latency.

SUMMARY OF THE INVENTION

The present invention is directed to a system and method of providing composite real-time dynamic imagery of a medical procedure site from multiple modalities which continuously and immediately depicts the current state and condition of the medical procedure site synchronously with respect to each modality and without undue latency. The composite real-time dynamic imagery may be provided by spatially registering multiple real-time dynamic video streams from the multiple modalities to each other. Spatially registering the multiple real-time dynamic video streams to each other may provide a continuous and immediate depiction of the medical procedure site with an unobstructed and detailed view of a region of interest at the medical procedure site. As such, a surgeon, or other medical practitioner, may view a single, accurate, and current composite real-time dynamic imagery of a region of interest at the medical procedure site as he/she performs a medical procedure, and thereby, may properly and effectively implement the medical procedure.

In this regard, a first real-time dynamic video stream of a scene based on a first modality may be received. A second real-time dynamic video stream of the scene based on a second modality may also be received. The scene may comprise tissues, bones, instruments, and/or other surfaces or objects at a medical procedure site and at multiple depths. The first real-time dynamic video stream and the second real-time dynamic video stream may be spatially registered to each other. Spatially registering the first real-time dynamic video stream and the second real-time dynamic video stream to each other may form a composite representation of the scene. A composite real-time dynamic video stream of the scene may be generated from the composite representation. The composite real-time dynamic video stream may provide a continuous and immediate depiction of the medical procedure site with an unobstructed and detailed view at multiple depths of a region of interest at the medical procedure site. The composite real-time dynamic video stream may be sent to a display.

The first real-time dynamic video stream may depict the scene from a perspective based on a first spatial state of a first video source. Also, the second real-time dynamic video stream may depict the scene from a perspective based on a second spatial state of a second video source. The first spatial state may comprise a displacement and an orientation of the first video source, while the second spatial state may comprise a displacement and an orientation of the second video source. The first spatial state and the second spatial state may be used to synchronously align a frame of the second real-time dynamic video stream depicting a current perspective of the scene with a frame of the first real-time dynamic video stream depicting a current perspective of the scene. In this manner, the displacement and orientation of the first video source and the displacement and orientation of the second video source may be used to accurately depict the displacement and orientation of the surfaces and objects in the scene from both of the current perspectives in the composite representation.

The first modality may be two-dimensional or three-dimensional. Additionally, the first modality may comprise endoscopy, and may be selected from a group comprising laparoscopy, hysteroscopy, thoroscopy, arthoscopy, colonoscopy, bronchoscopy, cystoscopy, proctosigmoidoscopy, esophagogastroduodenoscopy, and colposcopy. The second modality may be two-dimensional or three dimensional. Additionally, the second modality may comprise one or more modalities selected from a group comprising medical ultrasonography, magnetic resonance, x-ray imaging, computed tomography, and optical wavefront imaging. As such, a plurality, comprising any number, of video sources, modalities, and real-time dynamic video streams is encompassed by the present invention.

Those skilled in the art will appreciate the scope of the present invention and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the invention, and together with the description serve to explain the principles of the invention.

FIG. 1 is a schematic diagram illustrating an exemplary real-time dynamic imaging system, wherein a first real-time, dynamic video stream of a scene may be received from a first video source, and a second real-time dynamic video stream of the scene may be received from a second video source, and wherein the first real-time dynamic video stream and the second real-time dynamic video stream may be spatially registered to each other, according to an embodiment of the present invention;

FIG. 2 is a flow chart illustrating a process for generating a composite real-time dynamic video stream of the scene by spatially registering the first real-time dynamic video stream and the second real-time dynamic video stream according to an embodiment of the present invention;

FIGS. 3A, 3B, and 3C are graphical representations of the spatial registering of a frame of the first real-time dynamic video stream and a frame of the second real-time dynamic video stream to form a composite representation of the scene, according to an embodiment of the present invention;

Figure 7C:
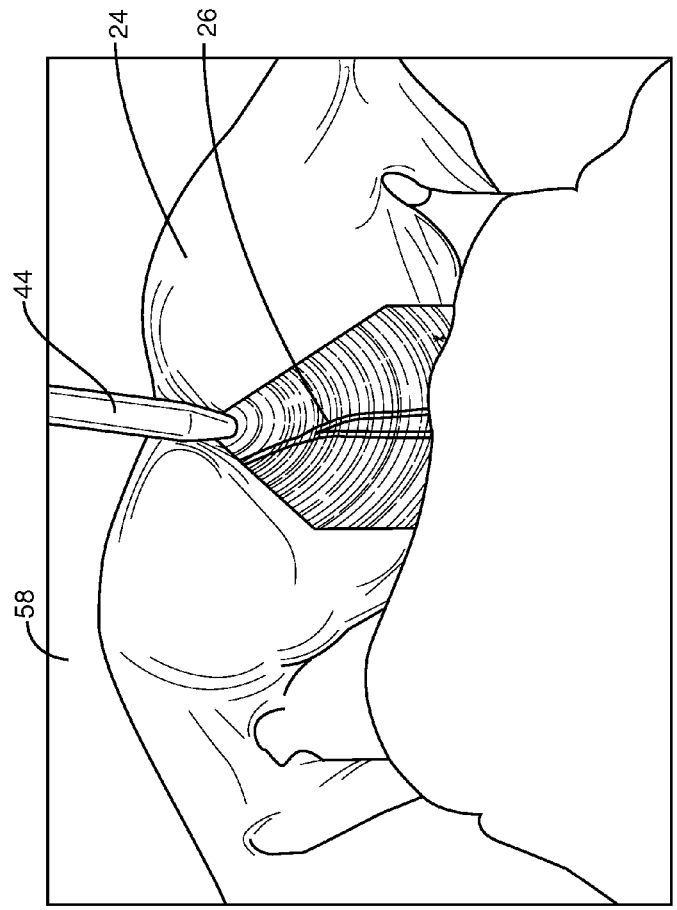
Figure 7A:
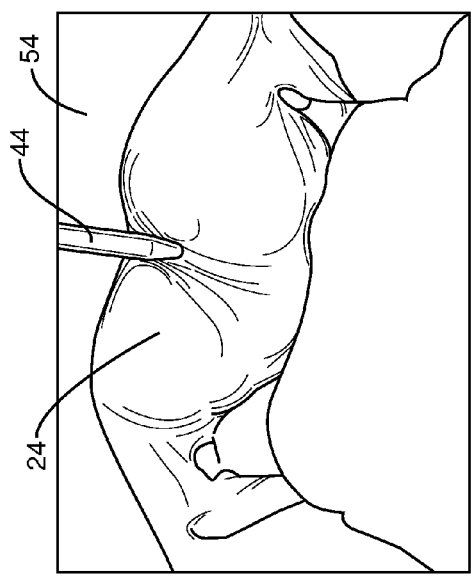
Figure 7B:
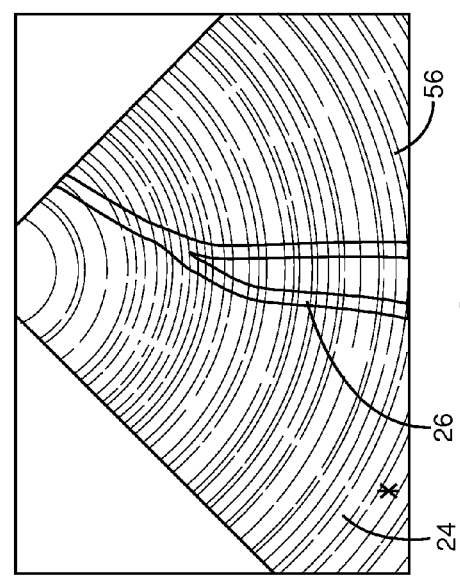
Figure 8:
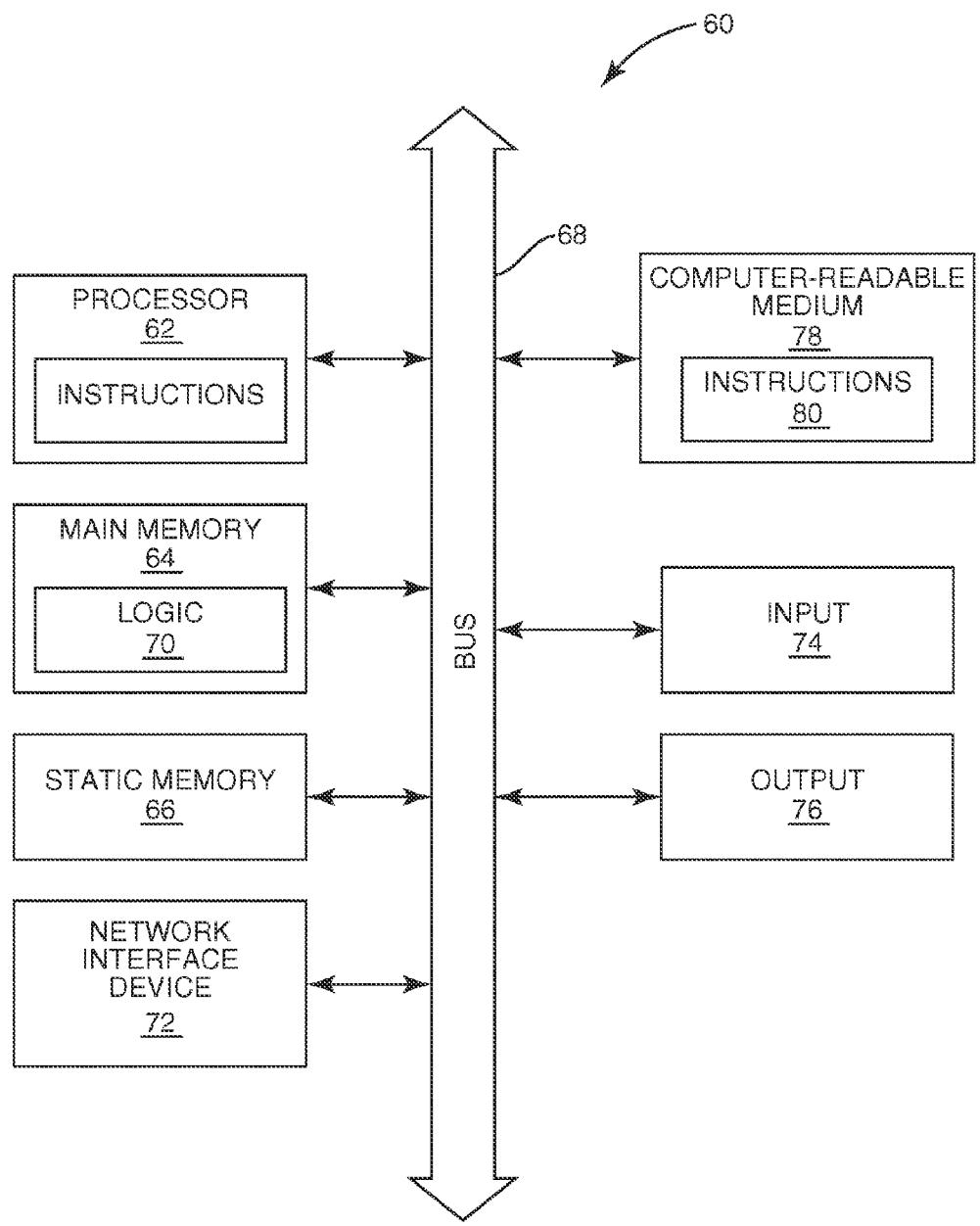

FIGS. 7A, 7B, and 7C are photographic representations of a frame from a laparoscopy-based real-time dynamic video stream, a frame of a two-dimensional medical ultrasonography-based real-time dynamic video stream, and a frame of a composite real-time dynamic video stream resulting from spatially registering the laparoscopy-based real-time dynamic video stream and the two-dimensional medical ultrasonography-based real-time dynamic video stream, according to an embodiment of the present invention; and FIG. 8 illustrates a diagrammatic representation of a controller in the exemplary form of a computer system adapted to execute instructions from a computer-readable medium to perform the functions for spatially registering the first real-time dynamic video stream and the second real-time dynamic video stream for generating the composite real-time dynamic video stream according to an embodiment of the present invention.

DETAILED DESCRIPTION OF THE PREFERRED EMBODIMENTS

The embodiments set forth below represent the necessary information to enable those skilled in the art to practice the invention and illustrate the best mode of practicing the invention. Upon reading the following description in light of the accompanying drawing figures, those skilled in the art will understand the concepts of the invention and will recognize applications of these concepts not particularly addressed herein. It should be understood that these concepts and applications fall within the scope of the disclosure and the accompanying claims.

The present invention is directed to a system and method of providing composite real-time, dynamic imagery of a medical procedure site from multiple modalities which continuously and immediately depicts the current state and condition of the medical procedure site synchronously with respect to each modality and without undue latency. The composite real-time dynamic imagery may be provided by spatially registering multiple real-time dynamic video streams from the multiple modalities to each other. Spatially registering the multiple real-time dynamic video streams to each other may provide a continuous and immediate depiction of the medical procedure site with an unobstructed and detailed view of a region of interest at the medical procedure site. As such, a surgeon, or other medical practitioner, may view a single, accurate, and current composite real-time dynamic imagery of a region of interest at the medical procedure site as he/she performs a medical procedure, and thereby, may properly and effectively implement the medical procedure.

In this regard, a first real-time dynamic video stream of a scene based on a first modality may be received. A second real-time dynamic video stream of the scene based on a second modality may also be received. The scene may comprise tissues, bones, instruments, and/or other surfaces or objects at a medical procedure site and at multiple depths. The first real-time dynamic video stream and the second real-time dynamic video stream may be spatially registered to each other. Spatially registering the first real-time dynamic video stream and the second real-time dynamic video stream to each other may form a composite representation of the scene. A composite real-time dynamic video stream of the scene may be generated from the composite representation. The composite real-time dynamic video stream may provide a continuous and immediate depiction of the medical procedure site with an unobstructed and detailed view at multiple depths of a region of interest at the medical procedure site. The composite real-time dynamic video stream may be sent to a display.

The first real-time dynamic video stream may depict the scene from a perspective based on a first spatial state of a first video source. Also, the second real-time dynamic video stream may depict the scene from a perspective based on a second spatial state of a second video source. The first spatial state may comprise a displacement and an orientation of the first video source, while the second spatial state may comprise a displacement and an orientation of the second video source. The first spatial state and the second spatial state may be used to synchronously align a frame of the second real-time dynamic video stream depicting a current perspective of the scene with a frame of the first real-time dynamic video stream depicting a current perspective of the scene. In this manner, the displacement and orientation of the first video source and the displacement and orientation of the second video source may be used to accurately depict the displacement and orientation of the surfaces and objects from both of the current perspectives in the composite representation.

The first modality may be two-dimensional or three-dimensional. Additionally, the first modality may comprise endoscopy, and may be selected from a group comprising laparoscopy, hysteroscopy, thoroscopy, arthoscopy, colonoscopy, bronchoscopy, cystoscopy, proctosigmoidoscopy, esophagogastroduodenoscopy, and colposcopy. The second modality may be two-dimensional or three dimensional. Additionally, the second modality may comprise one or more modalities selected from a group comprising medical ultrasonography, magnetic resonance, x-ray imaging, computed tomography, and optical wavefront imaging. As such, a plurality, comprising any number, of video sources, modalities, and real-time dynamic video streams is encompassed by embodiments of the present invention. Therefore, the first imaging modality may comprise a plurality of first imaging modalities and the second imaging modality may comprise a plurality of second imaging modalities.

Figure 1:
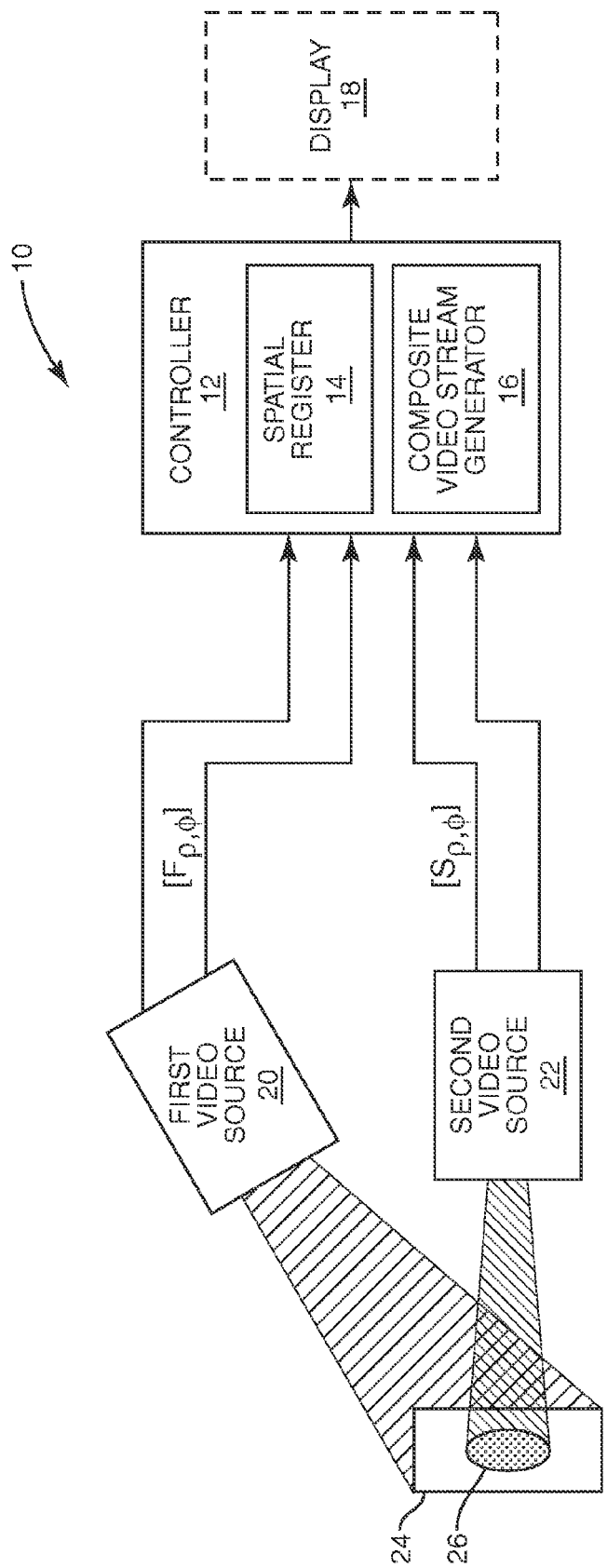
Figure 2:
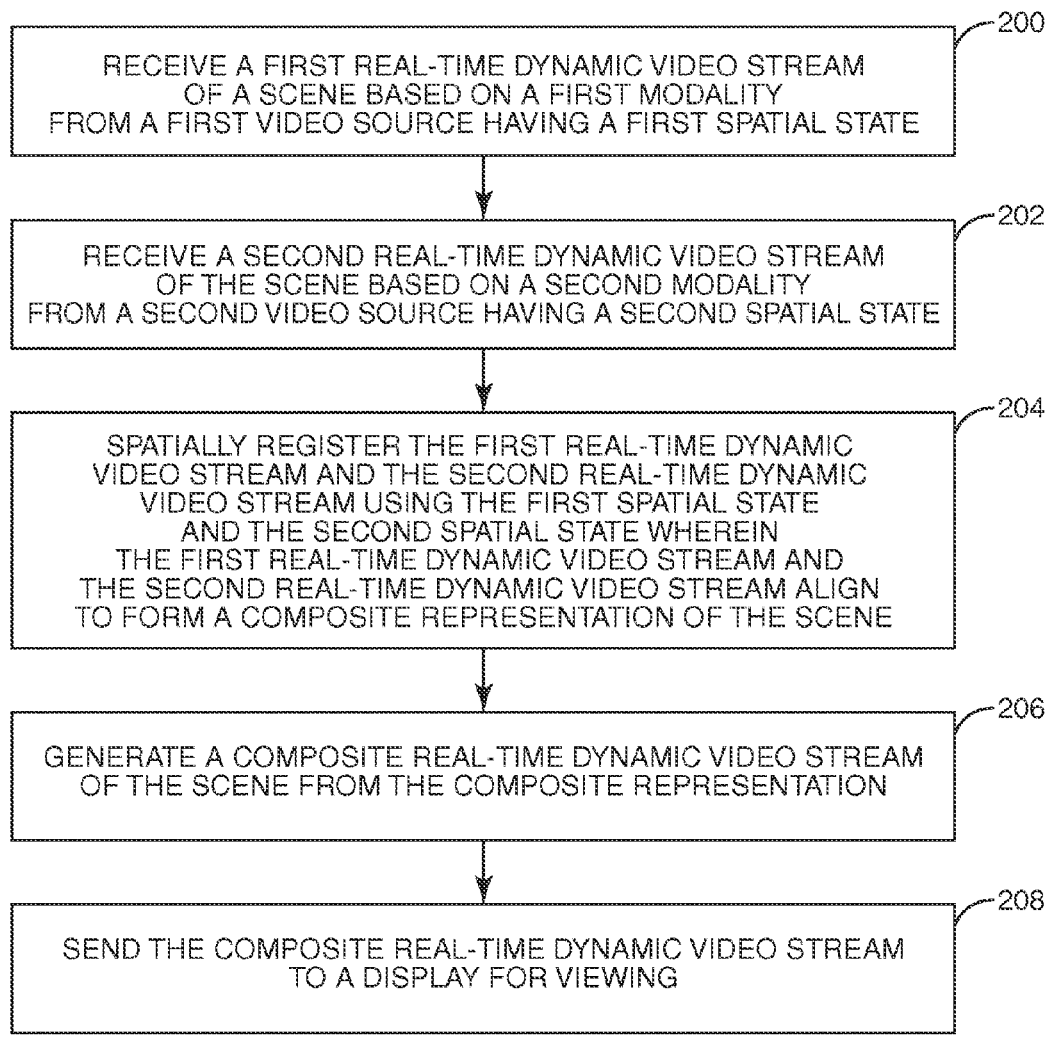

FIG. 1 illustrates a schematic diagram of an exemplary real-time dynamic imagery system 10 for generating a composite real-time dynamic video stream of a scene from a first real-time dynamic video stream based on a first modality and a second real-time dynamic video stream based on a second modality, according to an embodiment of the present invention. FIG. 2 is a flow chart illustrating a process for generating the composite real-time dynamic video stream of a scene in the system 10 according to an embodiment of the present invention. Using a first real-time dynamic video stream based on a first modality and a second real-time dynamic video stream based on a second modality to generate a composite real-time dynamic video stream may provide a continuous and immediate depiction of the current state and condition of the scene, and at multiple depths and with unobstructed depiction of details of the scene at those depths. For purposes of the embodiment of the present invention, immediate may be understood to be 500 milliseconds or less.

Accordingly, as the scene changes the first real-time dynamic video stream and the second real-time dynamic video stream may also change, and, as such, the composite real-time dynamic video stream may also change. As such, the composite real-time dynamic video stream may be immediate in that when viewed on a display, the composite real-time dynamic video stream may continuously depict the actual current state and/or condition of the scene and, therefore, may be suitable for medical procedure sites, including, but not limited to, surgical sites. By viewing a single, accurate, and current image of the region of interest, the surgeon, or the other medical practitioner, may properly and effectively implement the medical procedure while viewing the composite real-time dynamic imagery.

In this regard, the system 10 of FIG. 1 may include a controller 12 which may comprise a spatial register 14 and a composite video stream generator 16. The controller 12 may be communicably coupled, to a display 18, a first video source 20, and a second video source 22. The first video source 20 and the second video source 22 may comprise an instrument through which an image of the scene may be captured and/or detected. Accordingly, the first video source 20 and the second video source 22 capture and/or detect images of the scene from their particular perspectives. The first video source 20 may have a first spatial state and the second video source 22 may have a second spatial state. In this manner, the first spatial state may relate to the perspective in which the image is captured and/or detected by the first video source 20, and the second spatial state may relate to the perspective in which the image is captured and/or detected by the second video source 22.

The first spatial state may be represented as $[F_{\rho,\phi}]$, and the second spatial state may be represented as $[S_{\rho,\phi}]$. In FIG. 1, "$\rho$" may refer to three-dimensional displacement representing x, y, z positions, and "$\phi$" may refer to three-dimensional orientation representing roll, pitch, and yaw, with respect to both the first video source 20 and the second video source 22, as the case may be. By employing $[F_{\rho,\phi}]$ and $[S_{\rho,\phi}]$, the perspective of the first video source 20 viewing the scene and the perspective of the second video source 22 viewing the scene may be related to the three-dimensional displacement "$\rho$" and the three-dimensional orientation "$\phi$" of the first video source 20 and the second video source 22, respectively.

Accordingly, the first video source 20 and the second video source 22 capture and/or detect images of the scene from their particular perspectives. The scene may comprise a structure 24, which may be an organ within a person's body, and a region of interest 26 within the structure 24. The region of interest 26 may comprise a mass, lesion, growth, blood vessel, and/or any other condition and/or any detail within the structure 24. The region of interest 26 may or may not be detectable using visible light. In other words, the region of interest 26 may not be visible to the human eye.

The first video source 20 produces the first real-time dynamic video stream of the scene, and the second video source produces the second real-time dynamic video stream of the scene. The first real-time dynamic video stream of the scene may be a two-dimensional or three-dimensional video stream. Similarly, the second real-time dynamic video stream of the scene may be a two-dimensional or three-dimensional video stream.

FIG. 2 illustrates the process for generating a composite real-time dynamic video stream of the scene that may be based on the first real-time dynamic video stream and the second real-time dynamic video stream according to an embodiment of the present invention. The controller 12 may receive the first real-time dynamic video stream of a scene based on a first modality from a first video source having a first spatial state (step 200). The first modality may for example comprise two-dimensional or three-dimensional endoscopy. Additionally, the first modality may be any type of endoscopy such as laparoscopy, hysteroscopy, thoroscopy, arthoscopy, colonoscopy, bronchoscopy, cystoscopy, proctosigmoidoscopy, esophagogastroduodenoscopy, and colposcopy. The controller 12 also may receive the second real-time dynamic video stream of the scene based on a second medical modality from a second video source having a second spatial state (step 202). The second modality may comprise one or more of two-dimensional or three-dimensional medical ultrasonography, magnetic resonance imaging, x-ray imaging, computed tomography, and optical wavefront imaging. Accordingly, the present invention is not limited to only two video sources using two modalities to produce only two real-time dynamic video streams. As such, a plurality, comprising any number, of video sources, modalities, and real-time dynamic video streams is encompassed by the present invention.

The controller 12 using the spatial register 14 may then spatially register the first real-time dynamic video stream and the second real-time dynamic video stream using the first spatial state and the second spatial state to align the first real-time dynamic video stream and the second real-time dynamic video stream to form a real-time dynamic composite representation of the scene (step 204). The controller 12 using the composite video stream generator 16 may generate a composite real-time dynamic video stream of the scene from the composite representation (step 206). The controller 12 may then send the composite real-time dynamic video stream to a display 18.

Please note that for purposes of discussing the embodiments of the present invention, it should be understood that the first video source 20 and the second video source 22 may comprise an instrument through which an image of the scene may be captured and/or detected. In embodiments of the present invention in which an imaging device such as a camera, for example, may be fixably attached to the instrument, the first video source 20 and the second video source 22 may be understood to comprise the imaging device in combination with the instrument. In embodiments of the present invention in which the imaging device may not be fixably attached to the instrument and, therefore, may be located remotely from the instrument, the first video source 20 and the second video source 22 may be understood to comprise the instrument and not the imaging device.

Figure 3C:
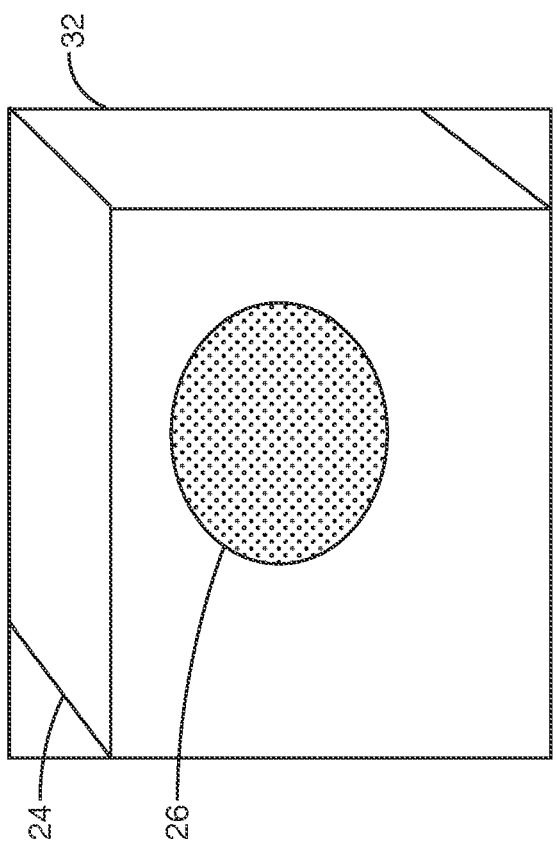
Figure 3A:
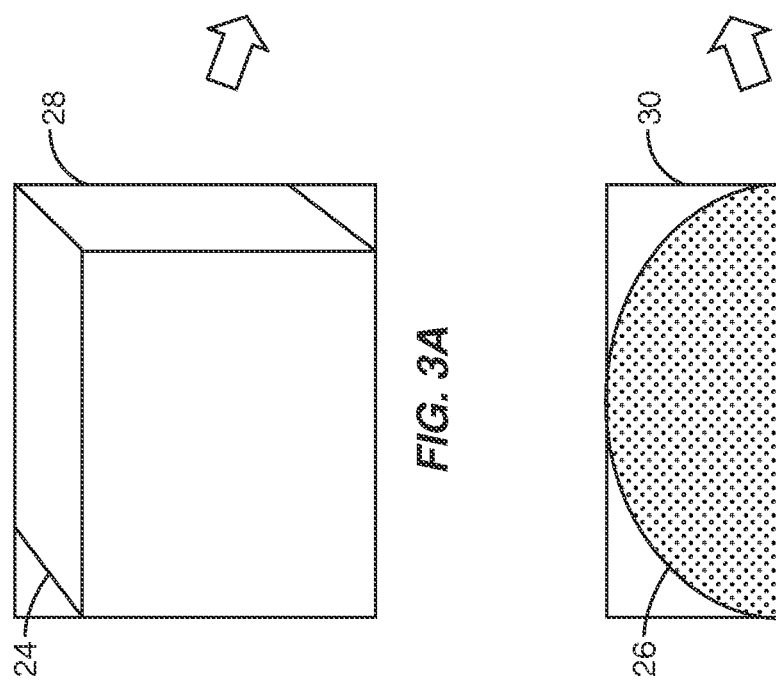
Figure 3B:
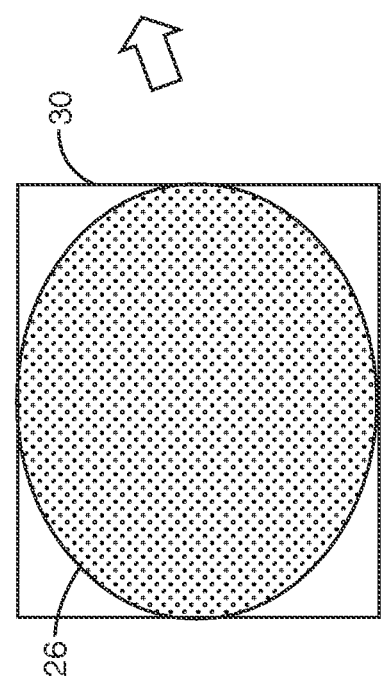

Spatially registering the first real-time dynamic video stream and the second real-time dynamic video stream may result in a composite real-time dynamic video stream that depicts the scene from merged perspectives of the first video source 20 and the second video source 22. FIGS. 3A, 3B, and 3C illustrate graphical representations depicting exemplary perspective views from the first video source 20 and the second video source 22, and a sequence which may result in the merged perspectives of the first real-time dynamic video stream and the second real-time dynamic video stream, according to an embodiment of the present invention. FIGS. 3A, 3B, and 3C provide a graphical context for the discussion of the computation involving forming the composite representation, which results from the spatial registration of the first real-time dynamic video stream and the second real-time dynamic video stream.

FIG. 3A may represent the perspective view of the first video source 20, shown as first frame 28. FIG. 3B may represent the perspective view of the second video source 22, shown as second frame 30. FIG. 3C shows the second frame 30 spatially registered with the first frame 28 which may represent a merged perspective and, accordingly, a composite representation 32, according to an embodiment of the present invention. The composite real-time dynamic video stream may be generated from the composite representation 32. Accordingly, the composite representation may provide the merged perspective of the frame of the scene depicted by the composite real-time dynamic video stream.

The first frame 28 may show the perspective view of the first video source 20 which may use a first medical modality, for example endoscopy. The first frame 28 may depict the outside of the structure 24. The perspective view of the structure 24 may fill the first frame 28. In other words, the edges of the perspective view of the structure 24 may be co-extensive and/or align with the corners and sides of the first frame 28. The second frame 30 may show the perspective view of the second video source 22 which may be detected using a second medical modality, for example medical ultrasonography. The second frame 30 may depict the region of interest 26 within the structure 24. As with the perspective view of the structure in the first frame 28, the perspective view of the region of interest 26 may fill the second frame 30. The edges of the region of interest 26 may be co-extensive and/or align with the sides of the second frame 30.

Because the perspective view of the structure 24 may fill the first frame 28, and the perspective view of the region of interest 26 may fill the second frame 30, combining the first frame 28 as provided by the first video source 20 with the second frame 30 as provided by the second video source 22 may not provide a view that accurately depicts the displacement and orientation of the region of interest 26 within the structure 24. Therefore, the first frame 28 and the second frame 30 may be synchronized such that the composite representation 32 accurately depicts the actual displacement and orientation of the region of interest 26 within the structure 24. The first frame 28 and the second frame 30 may be synchronized by determining the spatial relationship between the first video source 20 and the second video source 22 based on the first spatial state and the second spatial state. Accordingly, if the first spatial state and/or the second spatial state change, the first frame 28 and/or the second frame 30 may be synchronized based on the changed first spatial state and/or changed the second spatial state. In FIG. 3C, the first frame 28 and the second frame 30 may be synchronized by adjusting the second frame 30 to be co-extensive and/or aligned with the corners and the sides of the first frame 28. The spatial relationship may then be used to spatially register the second frame 30 with the first frame 28 to form the composite representation 32. The composite representation 32 may then depict the actual displacement and orientation of the region of interest 26 within the structure 24 synchronously with respect to the first real-time dynamic video stream and the second real-time video stream.

Spatially registering the first real-time dynamic video stream and the second real-time dynamic video stream may be performed using calculations involving the first spatial state of the first video source 20, and the second spatial state of the second video source 22. The first spatial state and the second spatial state each comprise six degrees of freedom. The six degrees of freedom may comprise a displacement representing x, y, z positions which is collectively referred to herein as "ρ," and orientation representing roll, pitch, and yaw which is collectively referred to herein as "φ." Accordingly, the first spatial state may be represented as $[F_{\rho,\phi}]$, and the second spatial state may be represented as $[S_{\rho,\phi}]$. The first special state and the second spatial state may be used to determine the spatial relationship between the first video source 20 and the second video source 22, which may be represented as $[C_{\rho,\phi}]$.

The first spatial state $[F_{\rho,\phi}]$ may be considered to be a transformation between the coordinate system of the first video source 20 and some global coordinate system G, and the second spatial state $[S_{\rho,\phi}]$ may be considered to be a transformation between the coordinate system of the second video source 22 and the same global coordinate system G. The spatial relationship $[C_{\rho,\phi}]$, then, may be considered as a transformation from the coordinate system of the second video source 22, to the coordinate system of the first video source 20.

As transforms, $[C_{\rho,\phi}]$, $[F_{\rho,\phi}]$, and $[S_{\rho,\phi}]$ may each be represented in one of three equivalent forms:

1) Three-dimensional displacement "ρ" as [tx, ty, tz] and three-dimensional orientation "φ" as [roll, pitch, yaw]; or
2) Three-dimensional displacement "ρ" as [tx, ty, tz] and three-dimensional orientation "φ" as a unit quaternion [qx, qy, qz, qw]; or
3) A 4-by-4 (16 element) matrix.

Form 1 has the advantage of being easiest to use. Form 2 has the advantage of being subject to less round-off error during computations, for example it avoids gimbal lock, a mathematical degeneracy problem. Form 3 is amendable to modern computer-graphics hardware, which has dedicated machinery for composing, transmitting, and computing 4-by-4 matrices.

In some embodiments, where the first video source 20 and second video source 22 do not move with respect to each other, the spatial relationship $[C_{\rho,\phi}]$ between the first video source 20 and the second video source 22 is constant and may be measured directly. Alternatively, if embodiments where the first video source 20 and the second video source 22 move relative to each other, the spatial relationship between the first video source 20 and the second video source 22 may be continually measured by a position detecting system. The position detecting system may measure an output $[C_{\rho,\phi}]$ directly, or it may measure and report the first spatial state $[F_{\rho,\phi}]$ the second spatial state $[S_{\rho,\phi}]$. In the latter case, $[C_{\rho,\phi}]$ can be computed as $[C_{\rho,\phi}]$ and $[C_{\rho,\phi}]$ as follows:

$$[C_{\rho,\phi}] = [F_{\rho,\phi}] * [S_{\rho,\phi}]^{-1} \text{ (indirect computation)}.$$

The three-dimensional position of the corner points of the second frame 30, relative to the center of the second frame 30, are constants which may be included in the specification sheets of the second video source 22. There are four (4) such points if the second video source 22 is two-dimensional, and eight (8) such points if the second video source 22 is three-dimensional. For each such corner point, three-dimensional position relative to the first video source 20 may be computed using the formula:

$$c_s = c_f * [C_{\rho,\phi}],$$

where $c_f$ is the second frame 30 corner point relative to the second video source 22, and $c_s$ is the second frame 30 corner point relative to first video source 20.

If either the first video source 20 or the second video source 22 comprise a video camera, then the field-of-view of the video camera, and the frame, may be given by the manufacturer. The two-dimensional coordinates of the corner points $(s_x, s_y)$ of the second frame 30 in the first frame 28 may be computed as follows:

$$c_{sp} = (c_s^*[P]),$$

$$\text{where } P = \begin{bmatrix} \cos(f) & 0 & 0 & 0 \\ 0 & \cos(f) & 0 & 0 \\ 0 & 0 & 0 & 0 \\ 0 & 0 & 1 & 0 \end{bmatrix},$$

and f=the field of view of the first video source 20.

$c_{sp}$ is a four (4) element homogenous coordinate consisting of $[x_{csp}, y_{csp}, z_{csp}, h_{csp}]$. The two-dimensional coordinates are finally computed as:

$$s_x = x_{csp}/h_{csp}; \text{ and}$$

$$s_y = y_{csp}/h_{csp}.$$

By knowing $s_x$ and $s_y$, for all the corners of the second frame 30 relative to the first frame 28 standard compositing hardware may be used to overlay and, thereby, spatially registering the first real-time dynamic video stream and the second real-time dynamic video stream to generate the composite real-time dynamic video stream. As such the spatial registration of the first real-time dynamic video stream and the second real-time dynamic video stream may be performed using information other than an anatomical characteristic and/or a position of the subject (i.e. a person's body), the world, or some other reference coordinate system. Accordingly, the composite real-time dynamic video stream may be generated independently of the position or condition of the subject, the location and/or existence of anatomical features and/or landmarks, and/or the condition or state of the medical procedure site.

The determination whether to directly or indirectly compute the spatial relationship between the first video source 20 and the second video source 22 may depend on an arrangement of components of the system, and a method used to establish the first spatial state of the first video source 20 and the second spatial state of the second video source 22.

Figure 4B:
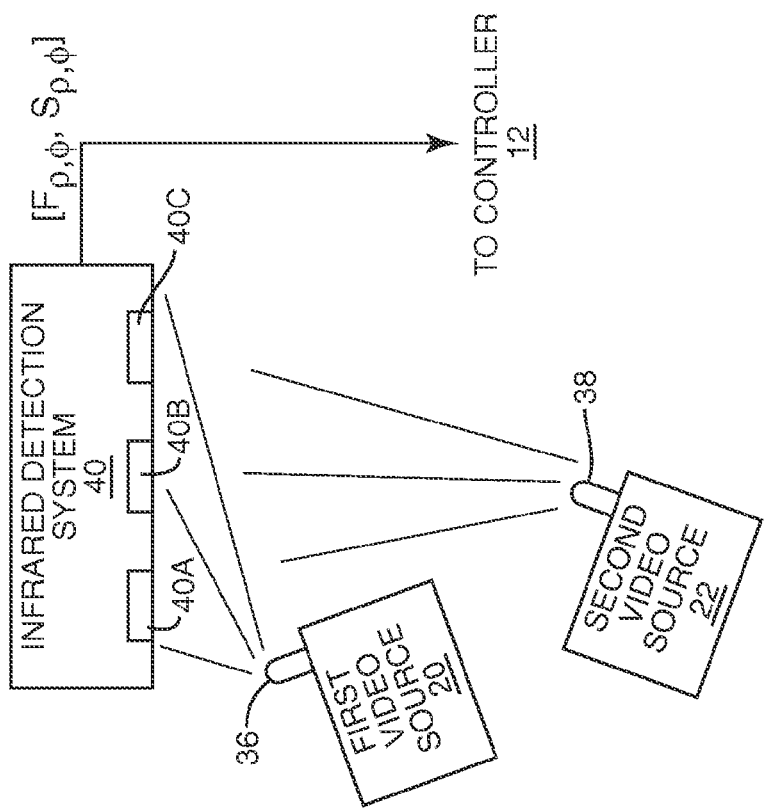
FIGS. 4A and 4B illustrate exemplary arrangements, which may be used to determine the spatial relationship between the first video source and the second video source using the first spatial state and the second spatial state, according to an embodiment of the present invention.
Figure 4A:
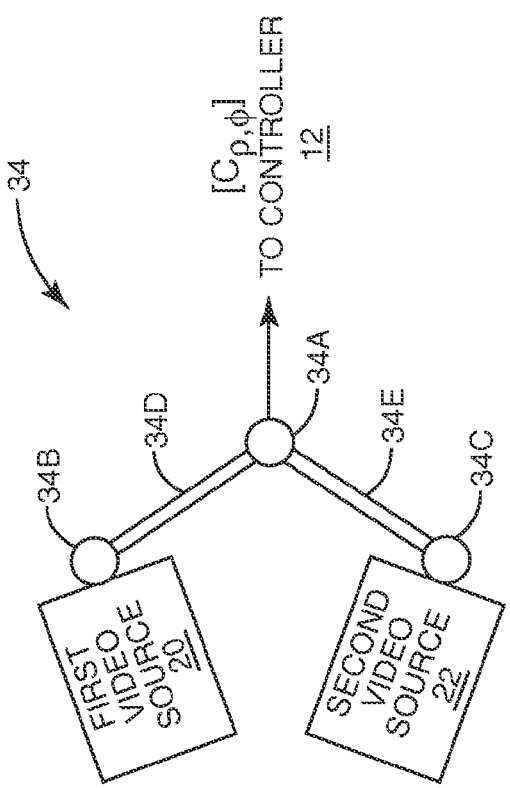

FIGS. 4A and 4B are schematic diagrams illustrating alternative exemplary arrangements of components in which the direct computation or the indirect computation for determining the spatial relationship between the first video source 20 and the second video source 22 may be used.

FIG. 4A illustrates an exemplary arrangement in which the direct computation of the spatial relationship between the first video source 20 and the second video source 22 may be used, according to an embodiment of the present invention. An articulated mechanical arm 34 may connect the first video source 20 and the second video source 22. The mechanical arm 34 may be part of and/or extend to an instrument or other structure, which supports and/or allows the use of the mechanical arm 34, and thereby the first video source 20 and the second video source 22. The mechanical arm 34 may provide a rigid connection between the first video source 20 and the second video source 22. In such a case, because the mechanical arm may be rigid, the first spatial state of the first video source 20 and the second spatial state of the second video source 22 may be fixed.

Accordingly, because the first spatial state and the second spatial state may be fixed, the first spatial state and the second spatial state may be programmed or recorded in the controller 12. The controller 12 may then directly compute the spatial relationship between the first video source 20 and the second video source 22 and, therefrom, the composite representation 32. As discussed above, the composite representation 32 represents the spatial registration of the first real-time dynamic video stream and the second real-time dynamic video stream. The controller 12 may then generate the composite real-time dynamic video stream from the composite representation 32.

Alternatively, the mechanical arm 34 may comprise joints 34A, 34B, 34C connecting rigid portions or links 34D, 34E of the mechanical arm 34. The joints 34A, 34B, 34C may include rotary encoders for measuring and encoding the angle of each of the joints 34A, 34B, 34C. By measuring the angle of the joints 34A, 34B, 34C and knowing the length of the links 34D, 34E, the first spatial state $[C_{\rho,\phi}]$ of the second video source 22, relative to that of the first video source 20 may be determined. The controller 12 may receive $[C_{\rho,\phi}]$ and, therefrom, compute the composite representation 32. As discussed above, the composite representation 32 represents the spatial registration of the first real-time dynamic video stream and the second real-time dynamic video stream. The controller 12 may generate the composite real-time dynamic video stream from the composite representation. The mechanical arm 34 may be a Faro-Arm™ mechanical arms or any similar component that provides the functionality described above.

FIG. 4B illustrates an exemplary arrangement where the indirect computation of the spatial relationship between the first video source 20 and the second video source 22 may be used, according to an embodiment of the present invention. In FIG. 4B, an intermediary in the form of a positions detecting system comprising a first transmitter 36, a second transmitter 38, and an infrared detection system 40 are shown. The first transmitter 36 and the second transmitter 38 may be in the form of LED's. The infrared detection system 40 may comprise one or more infrared detectors 40A, 40B, 40C. The infrared detectors 40A, 40B, 40C may be located or positioned to be in lines-of-sight of the first transmitter 36 and the second transmitter 38. The lines-of-sight are shown in FIG. 4B by lines emanating from the first transmitter 36 and the second transmitter 38.

The infrared detection system 40 may determine the first spatial state of the first video source 20 and the second spatial state of the second video source 22 by detecting the light emitted from the first transmitter 36 and the second transmitter 38, respectively. The infrared detection system 40 may also determine the intermediary reference related to the position of the infrared detection system 40. The infrared detection system 40 may then send the first spatial state of the first video source 20, represented as $[F_{\rho,\phi}]$, and the second spatial state of the second video source 22, represented as $[S_{\rho,\phi}]$, to the controller 12. The controller 12 may receive the first spatial state and the second spatial state, and may compute the spatial relationship $[C_{\rho,\phi}]$ between the first video source 20 and the second video source 22 using the indirect computation and, therefrom, the composite representation 32. As discussed above, the composite representation 32 represents the spatial registration of the first real-time dynamic video stream and the second real-time dynamic video stream. The controller 12 may then generate the composite real-time dynamic video stream from the composite representation 32.

The infrared detection system 40 may be any type of optoelectronic system for example the Northern Digital Instrument Optotrak™. Alternatively, other position detecting systems may be used such as magnetic, GPS+compass, inertial, acoustic, or any other equipment for measuring spatial relationship, or relative or absolute displacement and orientation.

Figure 5:
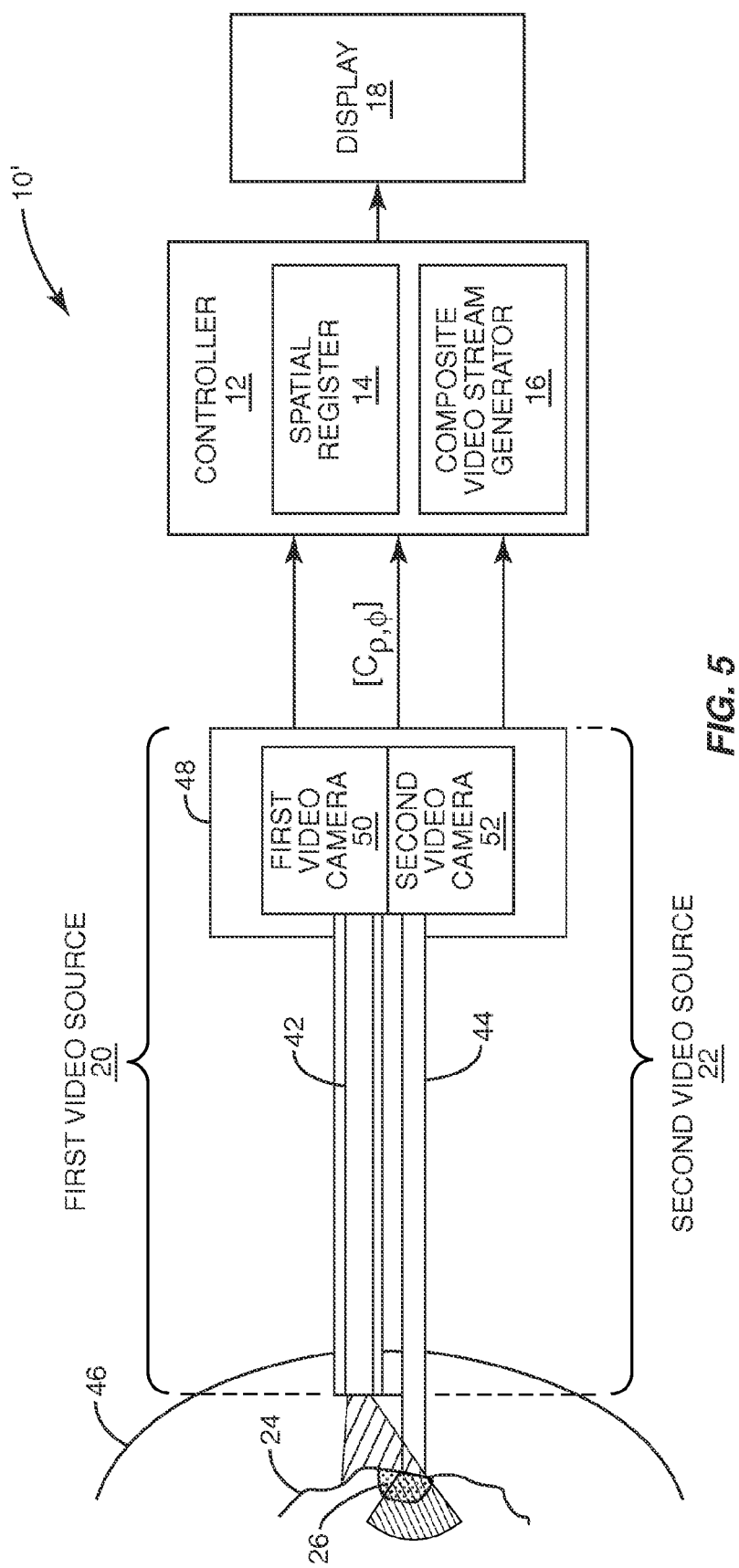
FIG. 5 is a schematic diagram illustrating an exemplary real-time dynamic imaging system at a medical procedure site, wherein the first video source and the second video source are co-located, and wherein the first video source may comprise an endoscope, and wherein the second video source may comprise an ultrasound transducer, according to an embodiment of the present invention.
Figure 6:
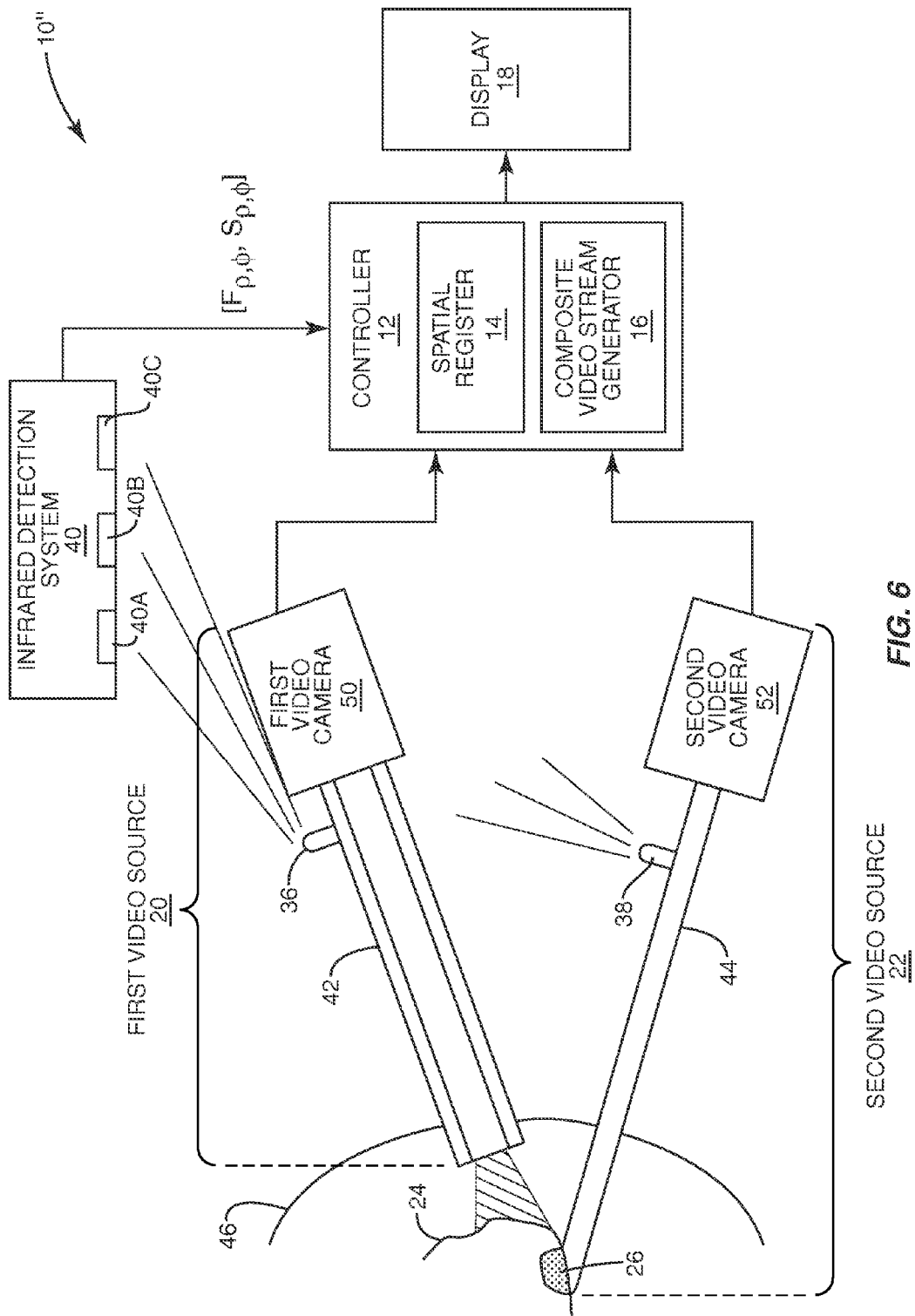
FIG. 6 is a schematic diagram illustrating an exemplary real-time dynamic imaging system at a medical procedure site wherein the first video source and the second video source are separately located and wherein an infrared detection system to determine the first spatial state and the second spatial state may be included, according to an embodiment of the present invention.

FIGS. 5 and 6 are schematic diagrams illustrating exemplary systems in which the exemplary arrangements discussed with respect to FIGS. 4A and 4B may be implemented in medical imaging systems based on the system 10 shown in FIG. 1, according to an embodiment of the present invention. FIGS. 5 and 6 each illustrate systems for generating composite real-time dynamic video streams using medical modalities comprising ultrasonography and endoscopy. Accordingly, FIGS. 5 and 6 comprise additional components and detail than which are shown in system 10 to discuss the present invention with respect to ultrasonography and endoscopy. However, it should be understood that the present invention is not limited to any particular modality, including any particular medical modality.

FIG. 5 is a schematic diagram illustrating a system 10' comprising an endoscope 42 and an ultrasound transducer 44 combined in a compound minimally-invasive instrument 48, according to an embodiment of the present invention. FIG. 5 is provided to illustrate an exemplary system in which the direct computation of the spatial relationship between the first video source 20 and the second video source 22 may be used. The compound minimally-invasive instrument 48 may be used to provide images of the scene based on multiple medical modalities using a single minimally-invasive instrument.

The compound minimally-invasive instrument 48 may penetrate into the body 46 of the subject, for example the patient, to align with the structure 24 and the region of interest 26 within the structure 24. In this embodiment, the structure 24 may be an organ within the body 46, and the region of interest 26 may be a growth or lesion within the structure 24. A surgeon may use the compound minimally-invasive instrument 48 to provide both an endoscopic and ultrasonogramic composite view to accurately target the region of interest 26 for any particular treatment and/or procedure.

The endoscope 42 may be connected, either optically or in some other communicable manner to a first video camera 50.

Accordingly, the first video source 20 may be understood to comprise the endoscope 42 and the first video camera 50. The first video camera 50 may capture an image of the structure 24 through the endoscope 42. From the image captured by the first video camera 50, the first video camera 50 may produce a first real-time dynamic video stream of the image and send the first real-time dynamic video stream to the controller 12.

The ultrasound transducer 44 may be communicably connected to a second video camera 52. Accordingly, the second video source 22 may be understood to comprise the ultrasound transducer 44 and the second video camera 52. The ultrasound transducer 44 may detect an image of the region of interest 26 within the structure 24 and communicate the image detected to the second video camera 52. The second video camera 52 may produce a second real-time dynamic video stream representing the image detected by the ultrasound transducer 44, and then send the second real-time dynamic video stream to the controller 12.

Because the compound minimally-invasive instrument 48 comprises both the endoscope 42 and the ultrasound transducer 44, the first spatial state and the second spatial state may be fixed with respect to each other, and, accordingly, the spatial relationship of the first video source 20 and the second video source 22 may be determined by the direct computation discussed above with reference to FIG. 4A. This may be so even if the first video camera 50 and the second video camera 52, as shown in FIG. 5, are located remotely from the compound minimally-invasive instrument 48. In other words, the first video camera 50 and the second video camera 52 may not be included within the compound minimally-invasive instrument 48. As discussed above, the first spatial state and the second spatial state may be determined relative to a particular perspective of the image of the scene that is captured and/or detected. As such the first spatial state may be based on the position and displacement of the endoscope 42, while the second spatial state may be based on the displacement and position of the ultrasound transducer 44.

The first spatial state and the second spatial state may be received by the controller 12. The controller 12 may then determine the spatial relationship between the first video source 20, and the second video source 22 using the direct computation discussed above. Using the spatial relationship, the first real-time dynamic video stream and the second real-time dynamic video stream may be spatially registered to generate the composite representation 32. The composite real-time dynamic video stream may be generated from the composite representation 32. The controller 12 may then send the composite real-time dynamic video stream to the display 18.

FIG. 6 is a schematic diagram illustrating a system 10" comprising a separate endoscope 42 and an ultrasound transducer 44, according to an embodiment of the present invention; in this embodiment, the endoscope 42 comprises a laparoscope, and the ultrasound transducer 44 comprises a laparoscopic ultrasound transducer. FIG. 6 is provided to illustrate an exemplary system in which the direct computation of the spatial relationship between the first video source 20 and the second video source 22 may be used.

Accordingly, in FIG. 6, instead of one minimally-invasive instrument penetrating the body 46, two minimally-invasive instruments are used. The endoscope 42 may align with the structure 24. The ultrasound transducer 44 may extend further into the body 46 and may contact the structure 24 at a point proximal to the region of interest 26. In a similar manner to the system 10', the structure 24 may be an organ within the body 46, and the region of interest 26 may be a blood vessel, growth, or lesion within the structure 24. A surgeon may use the endoscope 42 and the ultrasound transducer 44 to provide a composite view of the structure 24 and the region of interest 26 to accurately target the region of interest 26 point on the structure 24 for any particular treatment and/or procedure.

To provide one of the images of the composite view for the surgeon, the endoscope 42 may be connected, either optically or in some other communicable manner, to a first video camera 50. Accordingly, the first video source 20 may be understood to comprise the endoscope 42 and the first video camera 50. The first video camera 50 may capture an image of the structure 24 through the endoscope 42. From the image captured by the first video camera 50, the first video camera 50 may produce a first real-time dynamic video stream of the image and send the first real-time dynamic video stream to the controller 12.

Additionally, to provide another image of the composite view for the surgeon, the ultrasound transducer 44 may be communicably connected to a second video camera 52. Accordingly, the second video source 22 may be understood to comprise the ultrasound transducer 44 and the second video camera 52. The ultrasound transducer 44 may detect an image of the region of interest 26 within the structure 24 and communicate the image detected to the second video camera 52. The second video camera 52 may produce a second real-time dynamic video stream representing the image detected by the ultrasound transducer 44 and then send the second real-time dynamic video stream to the controller 12.

Because the endoscope 42 and the ultrasound transducer 44 are separate, the first spatial state of the first video source 20 and the second spatial state of the second video source 22 may be determined using the indirect computation discussed above with reference to FIG. 4B. As discussed above, the indirect computation involves the use of an intermediary, such as a positional system. Accordingly, in system 10", an intermediary comprising a first transmitter 36, a second transmitter 38 and an infrared detection system 40 may be included. The first transmitter 36 may be located in association with the endoscope 42, and the second transmitter 38 may be located in association with the ultrasound transducer 44. Associating the first transmitter 36 with the endoscope 42 and the second transmitter 38 with the ultrasound transducer 44 may allow the first video camera 50 to be located remotely from the endoscope 42, and/or the second video camera 52 to be located remotely from the ultrasound transducer 44.

As discussed above with respect to the system 10', the first spatial state and the second spatial state may be determined with respect to the particular perspectives of the image of the scene that may be captured and/or detected by the first video source 20 and the second video source 22, respectively. As such the first spatial state may be based on the orientation and displacement of the endoscope 42, while the second spatial state may be based on the displacement and orientation of the ultrasound transducer 44. Additionally, in system 10' of FIG. 5, the endoscope 42 and the ultrasound transducer 44 are shown in a co-located arrangement in the compound minimally-invasive instrument 48. As such, the first spatial state of the first video source 20 and the second spatial state of the of the second video source 22 in addition to being fixed may also be very close relationally. Conversely, in the system 10", the orientation and displacement of the endoscope 42 and the ultrasound transducer 44 may be markedly different as shown in FIG. 6, which may result in the first spatial state of the first video source 20 and the second spatial state of the second video source 22 not being close relationally.

The infrared detection system 40 may determine the first spatial state of the first video source 20 and the second spatial state of the second video source 22 by detecting the light emitted from the first transmitter 36 and the second transmitter 38, respectively. The infrared detection system 40 may also determine the intermediary reference related to the position of the infrared detection system 40. The infrared detection system 40 may then send the first spatial state, the second spatial state, and the intermediary reference to the controller 12. The controller 12 may receive the first spatial state, the second spatial state, and the intermediary reference and may compute the spatial relationship between the first video source 20 and the second video source 22 using the indirect computation and, therefrom, the composite representation 32. As discussed above, the composite representation 32 represents the spatial registration of the first real-time dynamic video stream and the second real-time dynamic video stream. The controller 12 may then generate the composite real-time dynamic video stream from the composite representation 32.

For purposes of the present invention, the controller 12 may be understood to comprise devices, components and systems not shown in system 10' and system 10" in FIGS. 5 and 6. For example, the controller 12 may be understood to comprise an ultrasound scanner, which may be a Sonosite MicroMaxx, or similar scanner. Also, the controller 12 may comprise a video capture board, which may be a Foresight Imaging Accustream 170, or similar board. An exemplary video camera suitable for use in the system 10' and system 10" of FIGS. 5 and 6 is the Stryker 988 that has a digital IEEE 1394 output, although other digital and analog cameras may be used. The endoscope may be any single or dual optical path laparoscope, or similar endoscope.

FIGS. 7A, 7B, and 7C are photographic representations illustrating a first frame 54 from the first real-time dynamic video stream, a second frame 56 from the second real-time dynamic video stream, and a composite frame 58 of the composite real-time dynamic video stream generated from the spatial registration of the first real-time dynamic video stream and the second real-time dynamic video stream, according to an embodiment of the present invention. FIGS. 7A, 7B, and 7C are provided to further illustrate an embodiment of the present invention with reference to actual medical modalities, and the manner in which the composite real-time dynamic video stream based on multiple modalities may appear to a surgeon viewing a display.

In FIG. 7A, the first real-time dynamic video stream may be produced based on an endoscopic modality. In FIG. 7B, the second real-time dynamic video stream may be produced based on medical ultrasonographic modality. In FIG. 7A, the first real-time dynamic video stream shows the structure 24 in the form of an organ of the human body being contacted by an ultrasound transducer 44. FIG. 7B shows the second real-time dynamic video stream is produced using the ultrasound transducer 44 shown in FIG. 7A. In FIG. 7B the region of interest 26, which appears as blood vessels within the structure 24 is shown. In FIG. 7C, the composite real-time dynamic video stream generated shows the first real-time dynamic video stream and the second real-time dynamic video stream spatially registered. The second real-time dynamic video stream is merged with the first real-time dynamic video stream in appropriate alignment. As such the second real-time dynamic video stream is displaced and oriented in a manner as reflects the actual displacement and orientation of the region of interest 26 within the structure 24. In other words, the region of interest 26 is shown in the composite real-time dynamic video stream as it would appear if the surface of the structure 24 were cut away to make the region of interest 26 visible.

FIG. 8 illustrates a diagrammatic representation of what a controller 12 adapted to execute functioning and/or processing described herein. In the exemplary form, the controller may comprise a computer system 60, within which is a set of instructions for causing the controller 12 to perform any one or more of the methodologies discussed herein. The controller may be connected (e.g., networked) to other controllers or devices in a local area network (LAN), an intranet, an extranet, or the Internet. The controller 12 may operate in a client-server network environment, or as a peer controller in a peer-to-peer (or distributed) network environment. While only a single controller is illustrated, the controller 12 shall also be taken to include any collection of controllers and/or devices that individually or jointly execute a set (or multiple sets) of instructions to perform any one or more of the methodologies discussed herein. The controller 12 may be a server, a personal computer, a mobile device, or any other device.

The exemplary computer system 60 includes a processor 62, a main memory 64 (e.g., read-only memory (ROM), flash memory, dynamic random access memory (DRAM) such as synchronous DRAM (SDRAM) or Rambus DRAM (RDRAM), etc.), and a static memory 66 (e.g., flash memory, static random access memory (SRAM), etc.), which may communicate with each other via a bus 68. Alternatively, the processor 62 may be connected to the main memory 64 and/or the static memory 66 directly or via some other connectivity means.

The processor 62 represents one or more general-purpose processing devices such as a microprocessor, central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. The processor 62 is configured to execute processing logic 70 for performing the operations and steps discussed herein.

The computer system 60 may further include a network interface device 72. It also may include an input means 74 to receive input (e.g., the first real-time dynamic video stream, the second real-time dynamic video stream, the first spatial state, the second spatial state, and the intermediary reference) and selections to be communicated to the processor 62 when executing instructions. It also may include an output means 76, including but not limited to the display 18 (e.g., a head-mounted display, a liquid crystal display (LCD), or a cathode ray tube (CRT)), an alphanumeric input device (e.g., a keyboard), and/or a cursor control device (e.g., a mouse).

The computer system 60 may or may not include a data storage device having a computer-readable medium 78 on which is stored one or more sets of instructions 80 (e.g., software) embodying any one or more of the methodologies or functions described herein. The instructions 80 may also reside, completely or at least partially, within the main memory 64 and/or within the processor 62 during execution thereof by the computer system 60, the main memory 64, and the processor 62 also constituting computer-readable media. The instructions 80 may further be transmitted or received over a network via the network interface device 72.

While the computer-readable medium is shown in an exemplary embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing, encoding, or carrying a set of instructions for execution by the controller and that cause the controller to perform any one or more of the methodologies of the present invention. The term "computer-readable medium" shall accordingly be taken to include, but not be limited to, solid-state memories, optical and magnetic media, and carrier wave signals.

Those skilled in the art will recognize improvements and modifications to the preferred embodiments of the present invention. All such improvements and modifications are considered within the scope of the concepts disclosed herein and the claims that follow.

What is claimed is:

1. A system for producing medical image guidance, comprising:
   a first device with which a first set of dynamic, real-time visual medical imaging data is related, wherein the first device's first spatial state is trackable using a spatial state tracking device;
   a second device with which a second set of dynamic, real-time medical imaging data is related, wherein the second device's second spatial state is trackable using the spatial state tracking device, wherein the second device is separate from and distinct from the first device; and
   an image guidance controller configured to:
      receive data related to the first spatial state of the first device;
      receive data related to the second spatial state of the second device;
      receive the first set of dynamic, real-time visual medical imaging data;
      receive the second set of dynamic, real-time medical imaging data;
      determine a relative spatial state of the first device and the second device based on the first device's first spatial state and the second device's second spatial state;
      produce combined dynamic, real-time image guidance data based on the first set of dynamic, real-time visual medical imaging data; the second set of dynamic, real-time medical imaging data; and the relative spatial state of the first device and the second device;
      wherein the first spatial state, the first set of dynamic, real-time visual medical imaging data, the second spatial state, and the second set of dynamic, real-time medical imaging data are each updated continually and the image guidance controller is configured to produce dynamic, real-time image guidance data continually.

2. The system of claim 1, wherein the dynamic, real-time image guidance data comprises a two-dimensional representation of the first set of dynamic, real-time visual medical imaging data and the second set of dynamic, real-time medical imaging data, combined based on the relative registration of one to the other in three-dimensional space based on the first and second spatial states.

3. The system of claim 1, wherein the continual updating and continual producing comprise updating and producing at least ten times per second.

4. The system of claim 1, wherein first set of dynamic, real-time visual medical imaging data comprises the ultrasound data captured by an ultrasound wand.

5. The system of claim 1, wherein second set of imaging data comprises a three-dimensional model related to the second device.

6. A system for producing medical image guidance, comprising:
   a first device with which a first set of dynamic, real-time visual medical imaging data is related, wherein the first device's first spatial state is tracked;
   a second device with which a second set of dynamic, real-time medical imaging data is related, wherein the second device's second spatial state is tracked, wherein the first device is separate from and distinct from the second device; and
   an image guidance controller configured to:
      determine the first device's first spatial state;
      determine the second device's second spatial state;
      determine the relative spatial states of the first device and the second device based on the first spatial state of the first device and the second spatial state of the second device; and
      produce dynamic, real-time image guidance data based on:
         the first set of dynamic, real-time visual medical imaging data;
         the second set of dynamic, real-time medical imaging data; and
         the relative spatial states of the first device and the second device,
      wherein the first spatial state, the first set of dynamic, real-time visual medical imaging data, the second spatial state, and the second set of dynamic, real-time medical imaging data are each updated continually and the image guidance controller is configured to produce dynamic, real-time image guidance data continually.

7. The system of claim 6, wherein the continual updating and continual producing comprise updating and producing at least ten times per second.

8. The system of claim 6, wherein first set of dynamic, real-time visual medical imaging data comprises the ultrasound data captured by an ultrasound wand.

9. The system of claim 6, wherein second set of imaging data comprises a three-dimensional model related to the second device.

10. The system of claim 6, wherein determining the first spatial state comprises receiving updates from spatial measurement equipment that is tracking the first device.

11. The system of claim 10, wherein the spatial measurement equipment comprises a tracker selected from the group consisting of an optical tracker and a magnetic tracker.

12. The system of claim 6, wherein the dynamic, real-time image guidance data comprises a two-dimensional representation of the first set of dynamic, real-time visual medical imaging data and the second set of dynamic, real-time medical imaging data, combined based on the relative registration of one to the other in three-dimensional space based on the first and second spatial states.

13. The system of claim 6, wherein first device comprises an ultrasound wand.

14. The system of claim 6, wherein second device comprises an ablation needle.

15. A system for producing medical image guidance, comprising:
   an input module configured to receive as input spatial states and data related to two or more tracked devices, wherein the two or more tracked devices comprise at least a first tracked device and a second tracked device the first tracked device is separate and distinct from the second tracked device, the input comprises at least a first spatial state of the first tracked device, a first set of dynamic, real-time visual medical imaging data related to the first tracked device, a second spatial state of the second tracked device, and a second set of dynamic, real-time medical imaging data related to the second tracked device, wherein the input module is configured to receive continually-updated input for the two or more tracked devices and the first spatial state, second spatial state, first set of dynamic, real-time visual medical imaging data, and second set of dynamic, real-time medical imaging data are continually updated;

an image guidance controller configured to process the input for the two or more tracked devices in order to produce combined dynamic, real-time displayable data, the processing comprising at least spatially registering the input for the first tracked device and the input for the second tracked device based on the first spatial state and the second spatial state and composing the first set of dynamic, real-time visual medical imaging data and the second set of dynamic, real-time medical imaging data based on the spatial registration; and an output module configured to transmit the combined dynamic, real-time displayable data to a display unit.

16. The system of claim 15, wherein the image guidance controller is configured to produce combined dynamic, real-time displayable data for each received, continually-updated input for the two or more tracked devices and the output module is configured to transmit the combined dynamic, real-time displayable data for each continually-updated input for the two or more tracked devices.

17. The system of claim 15, wherein the continually-updated input is updated at least ten times per second.

18. The system of claim 15, wherein the first set of dynamic, real-time visual medical imaging data comprises the ultrasound data captured by an ultrasound wand.

19. The system of claim 15, wherein second set of dynamic, real-time medical imaging data related comprises a three-dimensional model related to the second device.

20. The system of claim 15, wherein the first spatial state information is sent from spatial measurement equipment that is tracking the first device.

21. The system of claim 15, wherein the dynamic, real-time displayable data comprises a two-dimensional representation of the first set of dynamic, real-time visual medical imaging data and the second set of dynamic, real-time medical imaging data, combined based on the relative registration of one to the other in three-dimensional space based on the first and second spatial states.

22. The system of claim 15, wherein the first device comprises an ultrasound wand.

23. The system of claim 15, wherein the second device comprises an ablation needle.

24. A method for producing medical image guidance, comprising:

receiving at an imaging system electronic tracking data comprising a first spatial state of a first tracked device;

receiving at the imaging system electronic tracking data comprising a second spatial state of a second tracked device, wherein the second tracked device is separate and distinct from the first tracked device;

receiving at the imaging system a first set of dynamic, real-time visual medical imaging data related to the first tracked device;

receiving at the imaging system a second set of dynamic, real-time medical imaging data related to the second tracked device;

combining the first set of dynamic, real-time visual medical imaging data and the second set of dynamic, real-time medical imaging data into combined dynamic, real-time displayable data at the imaging system based on the first spatial state and second spatial state; and causing the display of the combined dynamic, real-time displayable data.

25. The method of claim 24, wherein the receiving electronic tracking data comprises continually receiving the tracking data.

26. The method of claim 24, wherein the image guidance wherein the dynamic, real-time displayable data comprises a two-dimensional representation of the first set of dynamic, real-time visual medical imaging data and the second set of dynamic, real-time medical imaging data, combined based on the relative registration of one to the other in three-dimensional space based on the first and second spatial states.

27. The method of claim 24, wherein the first set of dynamic, real-time visual medical imaging data comprises ultrasound data captured by an ultrasound wand.

28. The method of claim 24, wherein second set of dynamic, real-time medical imaging data related comprises a three-dimensional model related to the second device.

29. The method of claim 24, wherein the first device comprises an ultrasound wand and the second device comprises an ablation needle.

* * * * *

UNITED STATES PATENT AND TRADEMARK OFFICE
CERTIFICATE OF CORRECTION

| | | |
|---|---|---|
| PATENT NO. | : 7,728,868 B2 | |
| APPLICATION NO. | : 11/833134 | |
| DATED | : June 1, 2010 | |
| INVENTOR(S) | : Sharif A. Razzaque et al. | |

It is certified that error appears in the above-identified patent and that said Letters Patent is hereby corrected as shown below:

On Page 3, Col. 1, Line 23 under other publications change "Proceedigns" to -- Proceedings --.

On Page 3, Col. 2, Line 45, under other publications, change "(2000." to -- (2000). --.

On Page 4, Col. 1, Line 25, under other publications, change "intraepitheliallesions," to -- intraepithelial lesions, --.

On Page 14, Col. 3, Line 54, change "thoroscopy, arthoscopy," to -- thoracoscopy, arthroscopy, --.

On Page 15, Col. 6, Line 7, change "thoroscopy, arthoscopy," to -- thoracoscopy, arthroscopy, --.

On Page 16, Col. 7, Lines 44-45, change "thoroscopy, arthoscopy," to -- thoracoscopy, arthroscopy, --.

On Page 20, Col. 16, Line 57, after "medium" insert -- 78 --.

On Page 21, Col. 16, Line 59, in Claim 15, change "device" to -- device, --.

On Page 22, Col. 20, Line 27, after "claim 24," delete "wherein the image guidance".

Signed and Sealed this

Twenty-sixth Day of October, 2010

David J. Kappos
*Director of the United States Patent and Trademark Office*